US010136639B2

(12) United States Patent
Wuest et al.

(10) Patent No.: US 10,136,639 B2
(45) Date of Patent: *Nov. 27, 2018

(54) POLYCATIONIC AMPHIPHILES AS ANTIMICROBIAL AGENTS

(71) Applicants: TEMPLE UNIVERSITY OF THE COMMONWEALTH SYSTEM OF HIGHER EDUCATION, Philadelphia, PA (US); VILLANOVA UNIVERSITY, Philadelphia, PA (US)

(72) Inventors: William Wuest, Wallingford, PA (US); Kevin Patrick Minbiole, Media, PA (US)

(73) Assignees: Villanova University, Philadelphia, PA (US); Temple University of the Commonwealth System of Higher Education, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/034,375

(22) PCT Filed: Nov. 5, 2014

(86) PCT No.: PCT/US2014/064122
§ 371 (c)(1),
(2) Date: May 4, 2016

(87) PCT Pub. No.: WO2015/069764
PCT Pub. Date: May 14, 2015

(65) Prior Publication Data
US 2016/0262384 A1 Sep. 15, 2016

Related U.S. Application Data

(60) Provisional application No. 61/900,037, filed on Nov. 5, 2013, provisional application No. 62/039,265, filed
(Continued)

(51) Int. Cl.
*A01N 25/08* (2006.01)
*A01N 33/12* (2006.01)
(Continued)

(52) U.S. Cl.
CPC .............. *A01N 33/12* (2013.01); *A01N 25/08* (2013.01); *A61K 31/132* (2013.01); *Y02A 50/473* (2018.01)

(58) Field of Classification Search
None
See application file for complete search history.

(56) References Cited

U.S. PATENT DOCUMENTS 3,719,711 A   3/1973   Temple
6,093,564 A * 7/2000   Budowsky ............ A61L 2/0082
                                              424/184.1
(Continued)

FOREIGN PATENT DOCUMENTS

CN    101766972 A    7/2010
CS       229093 B1   5/1984
(Continued)

OTHER PUBLICATIONS

Wegrzynska et al. (Polish Journal of Chemical Technology (2006), 8(2), 59-61.*
(Continued)

*Primary Examiner* — Aradhana Sasan
(74) *Attorney, Agent, or Firm* — Duane Morris LLP

(57) ABSTRACT

The present disclosure provides an antimicrobial composition including a polycationic amphiphile compound, and the method of making and the method of using such a compound or composition. The compound having the formula (I) or (II) $R_1$, $R_2$, $R_3$, $R_4$, $R_5$, $R_6$, $R_{10}$, or $R_{11}$ is H or a $C_{1-12}$ alkyl unsubstituted or optionally substituted with a functional group such as —OH, —OR', —NH$_2$, —NHR', —NR'$_2$,
(Continued)

—N—C(O)R', —N—C(O)CR'=CR', —SH, —SR', —O—C(O)R', —C(O)R', —CF$_3$, —OCF$_3$, halogen, benzyl, o-vinylbenzyl, m-vinylbenzyl, p-vinylbenzyl, phenyl, allyl, and substituted allyl. R$_7$, R$_8$ or R$_9$ is a C$_{1-12}$ alkyl unsubstituted or optionally substituted with a functional group such as —OH, —OR', —NH$_2$, —NHR', —NR'$_2$, —SH, —SR', —O—C(O)R', —C(O)R', —CF$_3$, and —OCF$_3$. R' is H or a C$_{1-4}$ alkyl. X or Y is a halogen, m and n are integers in the range from 1 to 25.

25 Claims, 3 Drawing Sheets

Related U.S. Application Data on Aug. 19, 2014, provisional application No. 62/059,216, filed on Oct. 3, 2014.

(51) Int. Cl.
  *A01N 43/40* (2006.01)
  *A61K 31/132* (2006.01)
  *C07C 211/63* (2006.01)
  *C07C 323/25* (2006.01)
  *C07D 213/22* (2006.01)

(56) References Cited

U.S. PATENT DOCUMENTS

| | | |
|---|---|---|
| 6,358,914 B1 | 3/2002 | Gabriel et al. |
| 7,385,012 B2 | 6/2008 | Chang et al. |
| 2006/0025458 A1 | 2/2006 | Mamoun |
| 2014/0056951 A1 | 2/2014 | Losick et al. |
| 2014/0056952 A1 | 2/2014 | Losick et al. |
| 2016/0242413 A1* | 8/2016 | Wuest ............ A01N 33/12 |
| 2016/0278375 A1* | 9/2016 | Wuest ............ A61K 31/132 |

FOREIGN PATENT DOCUMENTS

| | | |
|---|---|---|
| DE | 1908980 | 2/1969 |
| FR | 1577286 A | 8/1969 |
| WO | 01/17357 A1 | 3/2001 |
| WO | 03/031407 A2 | 4/2003 |
| WO | 2008/015269 A1 | 2/2008 |

OTHER PUBLICATIONS

FR 1 577 286 (1969)—Original and English Machine Translation (7 pages).*

Forman, et al., "Building a Better Quaternary Ammonium Compound (QAC): Branched Tetracationic Antiseptic Annphiphiles," ChemMedChem, 2016, 11, pp. 1401-1405. (Year: 2016).*

Kourai, H. et al., "The Antimicrobial Characteristics of Quaternary Ammonium Salts", Antibact. Antifung. Agents, 1986,vol. 14, No. 2, pp. 55-63.

Brycki, Bogumil et al, "Synthesis, Molecular Structure, Spectral Properties and Antifungal Activity of Polymethylene-α,ω-bis(N,N-dimethyl-Ndodecyloammonium bromides", Molecules, 2011, vol. 16, 319-335.

Wang, X. et al., "Effects of structure dissymmetry on aggregation behaviors of quaternary ammonium Gemini surfactants in a protic ionic liquid EAN", Langmuir. Dec. 4, 2012;28(48) 16547-16554, Epub Nov. 16, 2012.

Kuperkar, K. et al., "Surface-Active Properties and Antimicrobial Study of Conventional Cationic and Synthesized Symmetrical Gemini Surfactants", J. Surfact Deterg, 2012, 15:107-115.

Mao, Xue-qiang et al., "Synthesis and Antibacterial Properties of Quaternary Ammonium Gemini Surfactants", Chinese Journal of Synthetic Chemistry, 2011, vol. 19, No. 2, pp. 180-183.

El Achouri, M. et al., "Gemini Surfactants of the Type 1,2-Ethanediyl bis-(dimethylalkylammonium bromide)", Tenside Surf. Det., Jul. 2001, 38(4), 208-215.

Zana, R. et al., "Alkanediyl-.alpha.,.omega.-bis(dimethylalkylammonium bromide) surfactants. 1. Effect of the spacer chain length on the critical micelle concentration and micelle ionization degree", Langmuir, 1991, 7, 1072-1075.

Imam, T., "Preparation and Antimicrobial Activity of Some New Bisquatenary Ammonium Salts", Pharmazie, May 1983, 38(5), 308-310.

Grenier, M.C. et al., "The antibacterial activity of 4,4'-bipyridinium amphiphiles with conventional, bicephalic and gemini architectures", Bioorg Med Chem Lett. Jun. 15, 2012;22(12):4055-8. Epub Apr. 25, 2012.

Ladow J.E. et al., "Bicephalic amphiphile architecture affects antibacterial activity", Eur J Med Chem. Sep. 2011;46(9):4219-26. Epub Jun. 25, 2011.

Devinsky, F. et al., "0uaternary ammonium-salts XVIII. Preparation and relationship between structure, IR spectral characteristics, and antimicrobial activity of some new bis-quatemary isosters of 1, 5-pentanediammonium dibromedes", Chemical Papers, (1987), vol. 41, No. 6, p. 803-814.

Tiecco, M. et al., "Biocidal and inhibitory activity screening of de novo synthesized surfactants against two eukaryotic and two prokaryotic microbial species", Colloids and Surfaces B: Biointerfaces, (Jun. 26, 2013), vol. 1111, p. 407-417.

International Search Report and Written Opinion issued in connection with International patent application No. PCT/US2014/064114, dated Feb. 4, 2015, 11 pages.

Findlay, B. et al., "Neomycin-phenolic conjugates: Polycationic amphiphiles with broad-spectrum antibacterial activity, low hemolytic activity and weak serum protein binding", Bioorganic & Medicinal Chemistry Letters, (2012), vol. 22, No. 4, p. 1499-1503.

Bera, S. et al., "Synthesis and antibacterial activities of amphiphilic neomycin B-based bilipid conjugates and fluorinated neomycin B-based lipids", Molecules, (2012), vol. 17, No. 8, p. 9129-9141.

Findlay, B. et al., "Cationic amphiphiles, a new generation of antimicrobials inspired by the natural antimicrobial peptide scaffold", Antimicrobial Agents and Chemotherapy, (2010), vol. 54, No. 10, p. 4049-4058.

Paniak, T. J. et al., "The antimicrobial activity of mono-, bis-, tris-, and tetracationic amphiphiles derived from simple polyamine platforms", Bioorganic & Medicinal Chemistry Letters, (Oct. 23, 2014), vol. 24, p. 5824-5828.

International Search Report and Written Opinion issued in connection with International patent application No. PCT/US2014/064122, dated Jan. 30, 2015, 5 pages.

Boncher, T. et al., "Polyamine-based analogues as biochemical probes and potential therapeutics", Biochemical Society Transactions, 2007, vol. 35, part 2, 356-363.

O'Toole, G.A. et al., "Diphosphonium Ionic Liquids as Broad Spectrum Antimicrobial Agents", Cornea, Jul. 2012, 31(7), 810-816.

Oda, R. et al., "Gemini surfactants, the effect of hydrophobic chain length and dissymmetry", Chem. Commun., 1997, 2105-2106.

Oda, R. et al., "Elongated Aggregares Formed by Cationic Gemini Surfactants", Langmuir, 1999, 15, 2384-2390.

Sikirić M. et al., "Effect of the spacer length on the association and adsorption behavior of dissymmetric gemini surfactants", Journal of Colloid and Interface Science, 281, (2005) 473-481.

Bai, G. et al., "Thermodynamics of Hydrophobic Interaction of Dissymmetric Gemini Surfactants in Aqueous Solutions", J. Phys. Chem. B, 2002, 106, 6614-6616.

Wang,, X. et al., "Micellization of a Series of Dissymmetric Gemini Surfactants in Aqueous Solution", J. Phys. Chem. B, 2003, 107, 11428-11432.

Fan, Y. et al, "Micellization of Dissymmetric Cationic Gemini Surfactants and Their Interaction with Dimyristoylphosphatidylcholine Vesicles", Langmuir, 2007, 23, 11458-11464.

Sun, Y. et al., "Adsorption of dissymmetric cationic gemini surfactants at silica/water interface", Surface Science, 601, 2007, 1988-1995.

(56) References Cited

OTHER PUBLICATIONS

Böttcher T. et al., "Synthesis and Activity of Biomimetic Biofilm Disruptors", Journal of the American Chemical Society, 2013, 135, 2927-2930.
Kolodkin-Gal, I. et al, "A Self-Producted Trigger for Biofilm Disassembly that Targets Exopolysaccharide", Cell, Apr. 27, 2012, 149, 684-392.
Almeida, J.A.S., "Dicationic Alkylammonium Bromid Gemini Surfactants. Membrane Perturbation and Skin Irritation", PLoS ONE, Nov. 2011, 6(11): e26965.
Romero, F.J. et al., "Room temperature synthesis of ordered porous silicas templated by symmetric and dissymmetric gemini surfactants [CnH2n+1N(CH2)2(CH3)2NCmH2m+1]Br2.", Microportous and Mesoporous Materials, 2004, 69(1-2): 43-48.
Sikiric, M. et al., "Adsorption and Association in Aqueous Solutions of Dissymmetric Gemini Surfactant", J. Colloid Interface Sci., 2002, 250(1): 221-229.
Sirvins, A. et al., "Bactericide compositions containing quaternary and diammonium alkyl salts", 1969, Societe Nationale des Petroles d'Aquitaine, English Abstract of French Patent No. 1577286, 2 pages.
Almeida, J.A.S. et al., "The effect of cationic gemini surfactants upon lipid membranes. An experimental and molecular dynamics simultation study", Phys. Chem. Chem. Phys., Jun. 2010, 12(43): 14462-14476.
Karlsson, L. et al., "Compaction of DNA by Gemini Surfactants: Effects of Surfactant Architecture", J. Colloid Interface Sci., 2002, 252(2): 290-296.
Cupcova, V. et al., "Inhibitory effect of 1-methyldodecyldemethylamine oxide and N,N-bis(dodecyldimethyl)-1,2-ethanediammonium dibromide on the spores of Bacillus cereus", Folia Microbiol (Praha), 1988, 33(6): 433-439.
Ciganekova, V. et al., "Effect of N,N'-bis (alkyldimethyl)-α,ω-alkanediammonium dibromides on bacteria of the genus *Clostridium*", Folio Microbiol. (Prague), 1989, 34(3): 202-208.
Ator, L.E., "Beyond paraquats: dialkyl 3,3'- and 3,4'-bipyridinium amphiphiles as antibacterial agents", Bioorg. Med. Chem. Lett. 2014, 3706-3709.
Walker, J.E., "The Germicidal Properties of Chemically Pure Soaps" J. Infect. Dis., Dec. 1924, 35(6), 557-566.
Devinsky, F. et al., "Quaternary ammonium salts XVIII. Preparation and relationship between structure, IR spectral characteristics, and antimicrobial activity of some new bis-quaternary isosters of 1,5-pentanediammonium dibromides" Chem. Papers, 1987, 41(6), 803-814.
Haldar, J. et al., "Synthesis and Antibacterial Properties of Novel Hydrolyzable Cationic Amphiphiles. Incorporation of Multiple Head Groups Leads to Impressive Antibacterial Activity" J. Med. Chem., 2005, 48, 3823-3831.
Maisuria, B.B. et al., "Comparing micellar, hemolytic, and antibacterial properties of di- and tricarboxyl dendritic amphiphiles" Bioorg. Med. Chem., 2011, 19, 2918-2926.
Tessema, T. et al., "Structure-activity relationships in aminosterol antibiotics: The effect of stereochemistry at the 7-OH group" Bioorg. Med. Chem. Lett., 2013, 23, 3377-3381.
Choomuenwai, V. et al., "The discovery, synthesis and antimalarial evaluation of natural product-based polyamine alkaloids" Tetrahedron Lett., 2013, 54, 5188-5191.
Liew, L.P.P. et al., "Synthesis and in vitro and in vivo evaluation of antimalarial polyamines" Eur. J. Med. Chem., 2013, 69, 22-31.
Khan, F.A. et al., "Syntheses of a library of molecules on the marine natural product ianthelliformisamines platform and their biological evaluation" Org. Biomol. Chem., Jun. 21, 2014, 12(23), 3757-4032.
Donkuru, M. et al., "Designing pH-sensitive gemini nanoparticles for non-viral gene delivery into keratinocytes" J. Mater. Chem., 2012, 22, 6232-6244.
Wettig, S.D. et al., "Thermodynamic and aggregation properties of aza- and imino-substituted gemini surfactants designed for gene delivery" Phys. Chem. Phys., 2007, 9, 871-877.
Wettig, S. D. et al., "Structural and transfection properties of amine-substituted gemini surfactant-based nanoparticles" J. Gene Med., 2007, 9, 649-658.
Zana, R. et al., "Micellization of Two Triquaternary Ammonium Surfactants in Aqueous Solution" Langmuir, 1995, 11, 3694-3698.
Pashirova, T. N. et al., "Supramolecular systems based on calix[4]resorcine with mono-, di-,and tetracationic surfactants: Synergetic structural and solubilization behavior" Colloids Surf., A, 2014, 448, 67-72.
Qian Guang-ren, "Surfactant scouring wastewater modified bentonites—promising material for unmanageable wastewater treatment" Journal of Shanghai University (English Edition), 2006, 10(1): 78-85.
Wang, L.-c. et al., "Synthesis of dissymmetric bis-quaternary ammonium salt surfactant", Zhengzhou Daxue Xuebao, Gongxueban, 2010, 31(3): p. 9-11, 15. [English Abstract Provided].
Kolodkin-Gal, I. et al., "Retraction Notice to: A Self-Producted Trigger for Biofilm Disassembly that Targets Exopolysaccharide" Cell, May 7, 2015, 161(4), 946.
Hobley, L. et al., "Norspermidine Is Not a Self-Produced Trigger for Biofilm Disassembly", Cell, Feb. 13, 2014, 156, 844-854.
Reiko Oda et al, "Gemini surfactants, effect of hydrophooic chain length and dissymmetry", Chemical Communications—ChemCom., vol. 21, Jan. 1, 1997 (Jan. 1, 1997), pp. 2105-2106, XP055358159.
Maja Sikiric et al, "Effect of the Spacer Length on the Solid Phase Transitions of Dissymmetric Gemini Surfactants", Langmuir, vol. 19, No. 24, Nov. 1, 2003 (Nov. 1, 2003), pp. 10044-10053, XP055358204.
Partial Supplementary European Search Report issued for corresponding European patent application No. 14860208.9, dated Apr. 4, 2017, 8 pages.
Extended European Search Report dated Jul. 21, 2017 in corresponding European Patent Application No. 14807857.9.
In, M. et al., "Quaternary Ammonium Bromide Surfactant Oligomers in Aqueous Solution: Self-Association and Microstructure", Langmuir, 1999, 16(1):141-148.
Danino, D. et al., "Branched Threadlike Micelles in an Aqueous Solution of a Trimeric Surfactant", Science, 1995, 269:1420-1421.
In, M. et al., "Growth and Branching of Charged Wormlike Micelles as Revealed by Dilution Laws", Langmuir, 2010, 26(13):10411-10414.
Zhi, C. et al., "Synthesis of Trimetric Cationic Surfactants", Chinese Journal of Synthetic Chemistry, 2010, 18(5):605-607, English Abstract provided.
Drummond, C. et al., "Reinforcement of a Surfactant Boundary Lubricant Film by a Hydrophilic-Hydrophilic Diblock Copolymer +", Langmuir, 2008, pp. 1560-1565.
Official Action dated Jul. 27, 2017 in corresponding Columbian Patent Application No. 16142381.
Extended European Search Report dated Apr. 4, 2017 in corresponding European Patent Application No. 14860700.5.

\* cited by examiner

POLYCATIONIC AMPHIPHILES AS ANTIMICROBIAL AGENTS

PRIORITY CLAIM AND CROSS-REFERENCE

This present application is a U.S. national phase application filed under 35 U.S.C. § 371 of International Application No. PCT/US2014/064122, which was filed Nov. 5, 2014, and which claims the benefit of U.S. Provisional Application No. 61/900,037, filed Nov. 5, 2013; U.S. Provisional Application No. 62/039,265, filed Aug. 19, 2014; and U.S. Provisional Application No. 62/059,216, filed Oct. 3, 2014, which applications are expressly incorporated by reference herein in their entireties.

FIELD

The disclosure relates to antimicrobial compositions and related methods. More particularly, the disclosed subject matter relates to a composition comprising a polycationic amphiphile, the method of making and the method of using such an amphiphile for antimicrobial use.

BACKGROUND

The preparation of chemical agents to counter the spread of human pathogens has been a challenge long before the term medicinal chemistry was coined. From the fermentation of beverages to the preparation of bleach, the facile production of compounds to minimize the pathogenic effects of microbes has been a key concern. Development of bacterial resistance to even the most potent antibiotics has ensured that continued research into antimicrobial compounds will remain crucial.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale.

SUMMARY OF THE INVENTION

Figure 1:
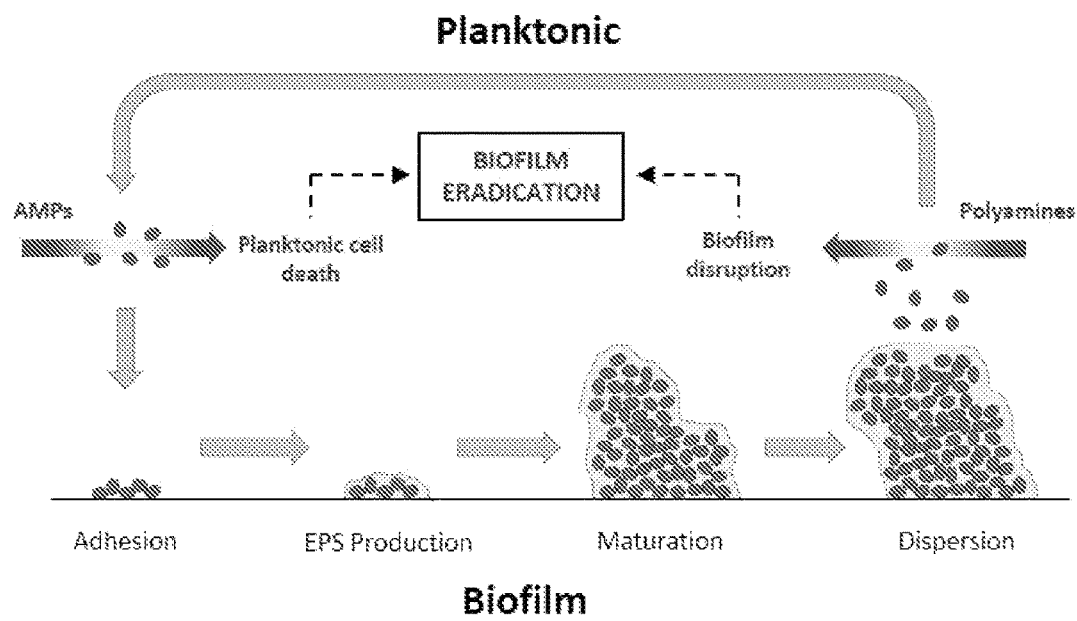
FIG. 1 illustrates the life cycle of a biofilm and the inspirations for developing polycationic amphiphiles to inhibit or eradicate biofilms in accordance with some embodiments.

This Summary is provided to present a summary of the invention to briefly indicate the nature and substance of the invention. It is submitted with the understanding that it will not be used to interpret or limit the scope or meaning of the claims.

The present disclosure provides an antimicrobial composition comprising a compound which is a polycationic amphiphile such as a triscationic or tetracationic amphiphile, the method of making such an antimicrobial composition, and the method of using such a compound or composition for antimicrobial use. The compound or the composition provided in the disclosure has an ability to kill or inhibit the growth of microorganisms, including but not limited to bacteria, viruses, yeast, fungi, and protozoa, to attenuate the severity of a microbial infection, or to inhibit formation of a biofilm or eradicate pre-established biofilms (i.e. antibiofilm use).

Some embodiments of the present disclosure provide an antimicrobial composition comprising a compound having the formula

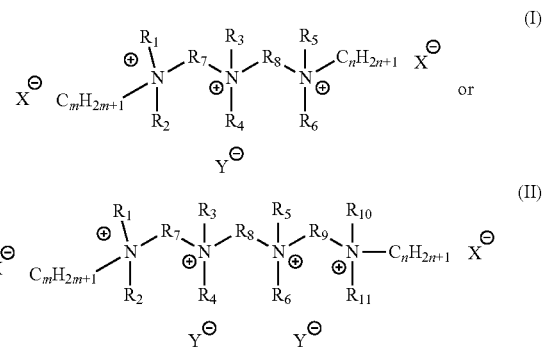

wherein:

$R_1$, $R_2$, $R_3$, $R_4$, $R_5$, $R_6$, $R_{10}$, or $R_{11}$ is H or a $C_{1-12}$ alkyl unsubstituted or optionally substituted with a functional group selected from the group consisting of —OH, —OR', —NH$_2$, —NHR', —NR'$_2$, —N—C(O)R', —N—C(O)CR'=CR', —SH, —SR', —O—C(O)R', —C(O)R', —CF$_3$, —OCF$_3$, halogen, benzyl, o-vinylbenzyl, m-vinylbenzyl, p-vinylbenzyl, phenyl, allyl, and substituted allyl;

$R_7$, $R_8$ or $R_9$ is a $C_{1-12}$ alkyl unsubstituted or optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$;

R' is H or a $C_{1-4}$ alkyl;

X or Y is a halogen (in the form of anion); and m and n are integers in the range from 1 to 25 (e.g., in the range from 10 to 16).

X or Y can be any halogen including but not limited to fluorine, chlorine, bromine, iodine, and any combination thereof. In some embodiments, $R_7$, $R_8$ or $R_9$ as the linkers between two nitrogen atoms can be a $C_{2-5}$ alkyl unsubstituted or optionally substituted. For example, linkers $R_7$, $R_8$ or $R_9$ can be —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—. In some embodiments, $R_1$, $R_2$, $R_3$, $R_4$, $R_5$, $R_6$, $R_{10}$, or $R_{11}$ may be a $C_{1-4}$ alkyl unsubstituted or optionally substituted. In some compounds, at least one of $R_1$, $R_2$, $R_3$, $R_4$, $R_5$, $R_6$, $R_{10}$, or $R_{11}$ is a $C_{1-12}$ alkyl substituted with a functional group selected from the group consisting of —SH, allyl, and substituted allyl.

In another aspect, the present disclosure provides a method of making the antimicrobial composition comprising a compound having the formula (I) or (II) as described. The method comprises mixing an effective amount of a compound having the formula (I) or (II) and a carrier.

The present disclosure also provides a method of killing or inhibiting microbial growth, comprising applying the antimicrobial composition comprising a compound having the formula (I) or (II) as described. The antimicrobial composition or the compound is used to kill or inhibit growth of at least one group of microorganisms selected from the group consisting of bacteria, viruses, yeast, fungi, and protozoa, or to inhibit formation of a biofilm, or disperse or eradicate a pre-established biofilm.

In another aspect, the present disclosure further provides a film or coating comprising a compound

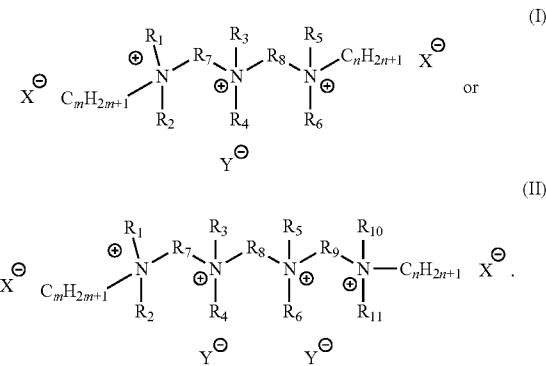

The compound having the formula (I) or (II) is grafted onto a solid surface. As described, $R_1$, $R_2$, $R_3$, $R_4$, $R_5$, $R_6$, $R_{10}$, or $R_{11}$ can be H or a $C_{1-12}$ alkyl (e.g., a $C_{2-5}$ alkyl) unsubstituted or optionally substituted with a functional group selected from the group consisting of —OH, —OR', —NH$_2$, —NHR', —NR'$_2$, —N=C(O)R', —N—C(O)CR'=CR', —SH, —SR', —O—C(O)R', —C(O)R', —CF$_3$, —OCF$_3$, halogen, benzyl, o-vinylbenzyl, m-vinylbenzyl, p-vinylbenzyl, phenyl, allyl, and substituted allyl. $R_7$, $R_8$ or $R_9$ can be a $C_{1-12}$ alkyl (e.g., a $C_{2-5}$ alkyl) unsubstituted or optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$. R' is H or a $C_{1-4}$ alkyl. X or Y is a halogen, including fluorine, chlorine, bromine, iodine and any combinations thereof. m and n are integers in the range from 1 to 25 (e.g., in the range from 10 to 16).

For example, the compound grafted on a solid surface may have a structure as shown by the formula

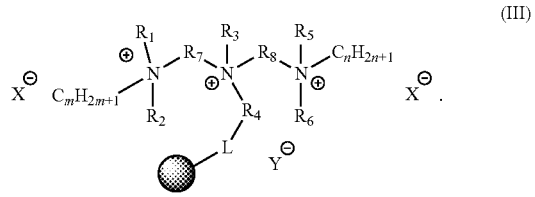

L is a linker comprising a functional group. In some embodiments, R4 is a methylene group optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$. In some embodiments, in such a film or coating comprising a compound having the formula (I) or (II), at least one of $R_1$, $R_2$, $R_3$, $R_4$, $R_5$, $R_6$, $R_{10}$, or $R_{11}$ is a $C_{1-12}$ alkyl substituted with a functional group (e.g., —SH, allyl, and substituted allyl).

The film or coating is configured to kill or inhibit growth of at least one group of microorganisms selected from the group consisting of bacteria, viruses, yeast, fungi, and protozoa, or to inhibit formation of a biofilm or eradicate pre-established biofilms.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "antimicrobial" refers to an ability to kill or inhibit the growth of microorganisms, including but not limited to bacteria, viruses, yeast, fungi, and protozoa, or to attenuate the severity of a microbial infection. The antimicrobial compounds or compositions of the present invention are compounds or compositions that may be used for cleaning or sterilization, or may be used in the treatment of disease and infection. The applications may include both in vitro and in vivo antimicrobial uses. "Applying" an antimicrobial composition may include administrating a composition into a human or animal subject.

The term "biofilm" as used herein refer to a film formed by a group of microorganisms adhered together. The term "antibiofilm" as used herein refer to an ability to kill, disperse and/or eradicate a pre-established biofilm.

The term "alkyl" as used herein refers to a straight chain, cyclic, branched or unbranched saturated or unsaturated hydrocarbon chain containing 1-25 carbon atoms, such as methyl, ethyl, propyl, tert-butyl, n-hexyl and the like. "A $C_{1-12}$ alkyl" as used herein refers to an alkyl group having a number of carbon atoms selected from 1 to 12.

The term "optionally substituted" means that group in question may be unsubstituted or it may be substituted one or several times, such as 1 to 3 times or 1 to 5 times. For example, an alkyl group that is "optionally substituted" with 1 to 5 chloro atoms, may be unsubstituted, or it may contain 1, 2, 3, 4, or 5 chlorine atoms. Substituted chemical moieties include one or more substituents that replace hydrogen.

The term "minimum inhibitory concentration (MIC)" means the lowest concentration of an antimicrobial agent that will inhibit the visible growth of a microorganism after overnight incubation. MIC values against bacteria, for example, the Gram-positive *Staphylococcus aureus* and *Enterococcus faecalis* and the Gram-negative *Escherichia coli* and *Pseudomonas aeruginosa* were determined by standard methods. See also P. A. Wayne, Methods for Dilution Antimicrobial Tests for Bacteria that Grow Aerobically; Approved Standard, Ninth Edition, 2012, CLSI Document M07-A9, Vol. 32 No. 2.

The term "the minimum biofilm eradication concentration (MBEC)" of a compound is defined as the lowest concentration of compound dosed against a previously established bacterial biofilm that leads to a clear well (optical density of less than 0.1) when the treated biofilm is regrown in fresh media, indicating >95% clearance of bacteria. A regrowth assay was used to establish the MBEC of a compound to evaluate the antibiofilm activity. See also H. Ceri, M. Olson, D. Morck, D. Storey, R. Read, A. Buret, B. Olson, *Methods Enzymol.* 2001, 337, 377.

The present disclosure provides an antimicrobial composition comprising a compound which is a polycationic (e.g., triscationic, tetracationic or the like) amphiphile, and the method of making such an antimicrobial compound or composition, and the method of using such a compound or composition for antimicrobial use. The compound or the composition provided in the disclosure has an ability to kill or inhibit the growth of microorganisms, including but not limited to bacteria, viruses, yeast, fungi, and protozoa, or to attenuate the severity of a microbial infection. The compound or the composition provided in the disclosure has an ability to inhibit or eradicate pre-established biofilms (i.e. antibiofilm use) formed by the microorganisms.

Biofilms are complex communities of bacteria that exist in a self-produced matrix of polysaccharides, proteins, and extracellular DNA. According to the US Centers for Disease Control and Prevention, biofilm infections are responsible for over 65% of nosocomial and foreign-device infections. Bacterial cells exhibiting the biofilm phenotype are 100-1000 times more resistant to standard antibiotics, as traditional molecular targets can be latent in the biofilm state and the presence of the extrapolymeric substance (EPS) interferes with antibiotic localization. As illustrated in FIG. 1, the biofilm life cycle consists of four stages: (1) Adhesion—planktonic cells undergo a phenotypic change and aggregate on a surface; (2) EPS production—secretion of polysaccharides, extracellular DNA, and proteins; (3) Maturation—development of biofilm architecture; and (4) Dispersion—phenotypic reversion to planktonic cells. Bacteria utilize many chemical signals to orchestrate this complex lifestyle, and significant efforts have been made to mimic these chemical classes to inhibit biofilm formation; however, synthetic compounds that eradicate pre-established biofilms have been sparsely reported.

Amphiphiles, molecules with both polar and non-polar regions, have been a mainstay of antimicrobial compounds. The use of soap, with ready availability and a simple anionic amphiphilic structure, has developed into one of the greatest advances in human health. The use of benzalkonium chloride, with a comparably straightforward cationic amphiphilic structure, propelled this revolution into the 20$^{th}$ century, where a number of amphiphilic compositions such as LYSOL® brand products have become commonplace in the household.

Because a variety of amphiphiles share a common method of action, namely membrane disruption, both anionic and cationic versions have been the focus of antimicrobial development campaigns in recent decades. Cationic amphiphiles have been regarded as membrane disruptors, capitalizing on electrostatic interactions with the predominantly anionic bacterial cell membrane, followed by intercalation of the non-polar chain, which leads to membrane disruption and ultimately bacterial cell lysis. Multiply charged amphiphilic species having polyanionic structures have been developed, perhaps taking inspiration from nature's antimicrobial peptides. For example, a series of dendritic amphiphiles having three carboxylate groups allow for attachment to surfaces (Scheme 1, left).

Scheme 1

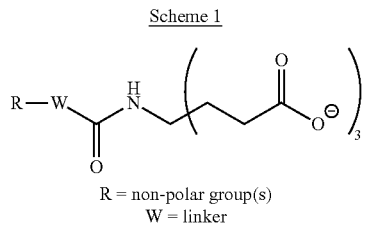

R = non-polar group(s)
W = linker

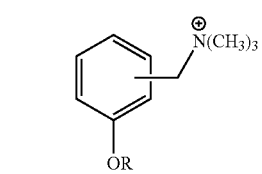

A

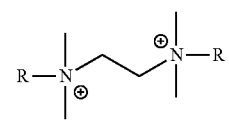

B

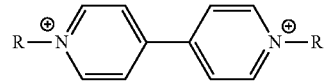

C

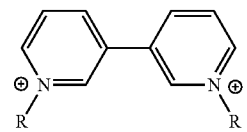

D

The inventors have developed cationic amphiphilic structures and have correlated the structures to antimicrobial activity. The inventors have developed quaternary ammonium amphiphiles based on an all-carbon aromatic core (A), an inexpensive TMEDA (N,N,N',N'-tetramethyl ethylenediamine) core (B), as well as bis-pyridinium structures of both 4,4' (C) and other geometries (D), as illustrated in Scheme 1. The inventors have further developed a series of novel polycationic (e.g., triscationic, tetracationic or the like)

amphiphile compounds for antimicrobial uses in the present disclosure. These compounds can be used in an antimicrobial composition, or used as a film or coating after grated onto a solid surface.

In one aspect, the present disclosure provides an antimicrobial composition comprising a compound having the formula

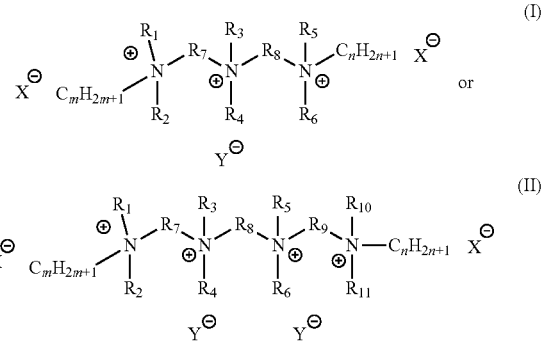

wherein:

$R_1$, $R_2$, $R_3$, $R_4$, $R_5$, $R_6$, $R_{10}$, or $R_{11}$ is H or a $C_{1-12}$ alkyl unsubstituted or optionally substituted with a functional group such as —OH, —OR', —NH$_2$, —NHR', —NR'$_2$, —N—C(O)R', —N—C(O)CR'═CR', —SH, —SR', —O—C(O)R', —C(O)R', —CF$_3$, —OCF$_3$, halogen, benzyl, o-vinylbenzyl, m-vinylbenzyl, p-vinylbenzyl, phenyl, allyl, and substituted allyl;

$R_7$, $R_8$ or $R_9$ is a $C_{1-12}$ alkyl unsubstituted or optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$;

R' is H or a $C_{1-4}$ alkyl or optionally substituted;

X or Y is a halogen (in the form of anion); and m and n are integers in the range from 1 to 25.

For example, in some embodiments, $R_1$, $R_2$, $R_3$, $R_4$, $R_5$, $R_6$, $R_{10}$, or $R_{11}$ can be H or a $C_{1-4}$ alkyl unsubstituted or optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$. In some embodiments, at least one of $R_1$, $R_2$, $R_3$, $R_4$, $R_5$, $R_6$, $R_{10}$, or $R_{11}$ is a $C_{1-12}$ alkyl substituted with a functional group such as —SH, allyl, substituted allyl or the like. X or Y can be any halogen in the form of ion including but not limited to fluorine, chlorine, bromine, iodine, and any combination thereof. X or Y can be also tosylate, citrate, any suitable anions or combinations thereof. In some embodiments, X or Y is chlorine or bromine (i.e. chloride or bromide). m and n can be integers in the range from 5 to 25 (e.g., in the range from 10 to 16). m can be equal or not equal to n. For example, in some embodiments, at least one of m and n is 12.

$R_7$, $R_8$ or $R_9$ as the linkers between two nitrogen atoms can be a $C_{2-5}$ alkyl unsubstituted or optionally substituted. $R_7$, $R_8$ or $R_9$ may be a repeating methylene group unsubstituted in the form of —(CH$_2$)$_s$—, or optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$, s is an integer, for example, in the range from 1 to 12. The value of s in $R_7$, $R_8$ or $R_9$ can be different from each other.

In some embodiments, linkers $R_7$, $R_8$ or $R_9$ is —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—. For example, the compound having the formula (I) can have the formula

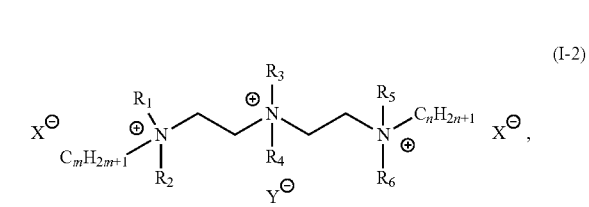

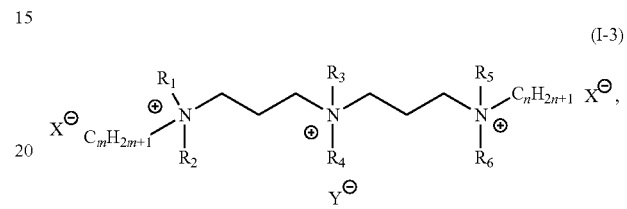

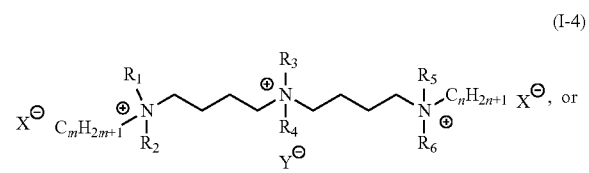

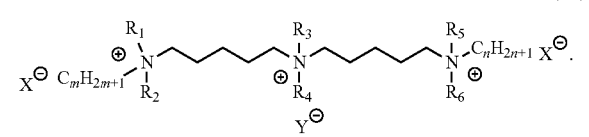

In the compound having the formula (I-2), (I-3), (I-4) or (I-5) (e.g., I-3), at least one of $R_1$ and $R_2$, and at least one of $R_3$ and $R_4$, and at least one of $R_5$ and $R_6$, can be methyl in some embodiments. In some of these compounds, m and n are 12, one of $R_3$ and $R_4$ is selected from a group consisting of ethyl, propyl and allyl, and the other groups among $R_1$, $R_2$, $R_3$, $R_4$, $R_5$, and $R_6$ are methyl.

Some exemplary compounds described in the present disclosure are denoted using a combination of numbers. For example, in some compounds having the formula (I-2), (I-3), (I-4) or (I-5), both $R_1$ and $R_2$, both $R_5$ and $R_6$ are methyl. At least one of $R_3$ and $R_4$ is methyl. Assuming $R_3$ is methyl, $R_4$ is H or an alkyl having x carbons, which is substituted or optionally substituted. Such a compound is denoted as compound [m, s, x, s, n], compound (m, s, x, s, n), or compound m, s, x, s, n. x is the carbon number of carbon atoms in $R_4$. When $R_4$ is H, x is zero. For example, such a compound having the formula (I-3), in which $R_3$ is methyl, $R_4$ is ethyl and both m and n are 12, is denoted as compound [12, 3, 2, 3, 12]. When $R_4$ is an allyl group, x is denoted as "3A." For example, such a compound having the formula (I-3), in which $R_3$ is methyl, $R_4$ is allyl and both m and n are 12, is denoted as compound [12, 3, 3A, 3, 12].

Similarly, the compound having the formula (II) can have the formula

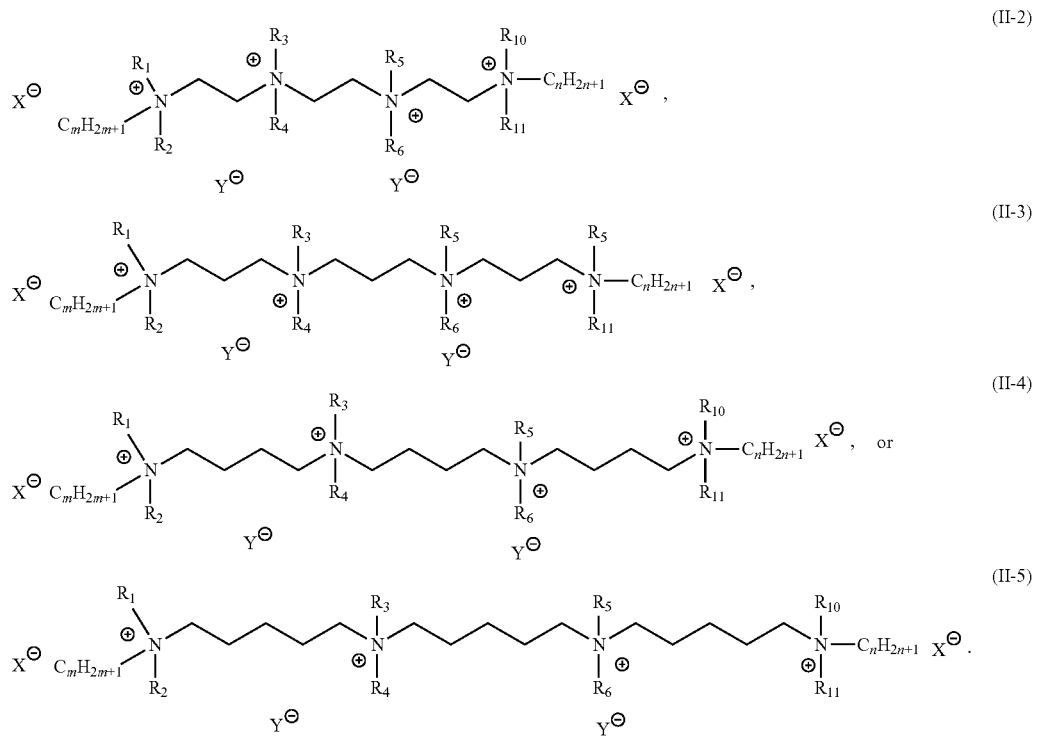

In the compound having the formula (II-2), (II-3), (II-4) or (II-5), at least one of $R_1$ and $R_2$, and at least one of $R_3$ and $R_4$, at least one of $R_5$ and $R_6$, and at least one of $R_{10}$ and $R_{11}$ can be methyl in some embodiments. In some of these compounds, for example, having the formula (II-2), m and n are 12, one of $R_3$ and $R_4$ is selected from a group consisting of ethyl, propyl and allyl, and the other groups among $R_1$, $R_2$, $R_3$, $R_4$, $R_5$, $R_6$, $R_{10}$, and $R_{11}$ are methyl.

Some exemplary compounds described in the present disclosure are denoted using a combination of numbers. For example, in some compounds having the formula (II-2), both $R_1$ and $R_2$, and both $R_{10}$ and $R_{11}$ are methyl. At least one of $R_3$ and $R_4$ is methyl. At least one of $R_5$ and $R_6$ is methyl. Assuming $R_3$ and $R_5$ are methyl, $R_4$ and $R_6$ are H or an alkyl having $x_4$ and $x_6$ carbons, respectively, which is substituted or optionally substituted. Such a compound is denoted as compound [N4-m, $x_4$, $x_6$, n], compound (N4-m, $x_4$, $x_6$, n), or compound N4-m, $x_4$, $x_6$, n. When $R_4$ or $R_6$ is H, $x_4$ or $x_6$ is zero. For example, such a compound having the formula (II-2), in which $R_3$ and $R_5$ are methyl, $R_4$ and $R_6$ are methyl, and both m and n are 12, is denoted as compound [N4-12, 1, 1, 12]. When $R_4$ and $R_6$ are an allyl group, $x_4$ or $x_6$ are denoted as "3A." For example, such a compound having the formula (II-2), in which $R_3$ and $R_5$ are methyl, $R_4$ and $R_6$ are allyl, and both m and n are 12, is denoted as compound [N4-12, 3A, 3A, 12].

The present disclosure also provides a method of making a compound having the formula (I) or (II) as described. Synthesis of the compound having the formula (I) or (II) can be achieved using a corresponding polyamine, particularly a polyamine with desirable cost. The polyamine can be grafted with the substitution groups at both ends or in the middle to form the resulting polycationic compound.

In another aspect, the present disclosure provides a method of making the antimicrobial composition compris-ing a compound having the formula (I) or (II) as described. The method comprises mixing an effective amount of a compound having the formula (I) or (II) and a carrier such as a solvent, a carrier, an additive, any other suitable ingredient, or combinations thereof.

In some embodiments, the present disclosure also provides an antimicrobial composition comprising a compound having the formula (I) or (II) as described, and a carrier such as a solvent. The antimicrobial composition can also comprise other ingredients and additives. The content of the compound having the formula (I) or (II) can be in any suitable concentration. For example, in some embodiments, such a concentration can be in the range from 0.01 μM to 100 μM, for example, from 0.1 μM to 10 μM. In some embodiments, the content of the compound having the formula (I) or (II) may be at a concentration of from 0.1 wt. % to 5 wt. %, for example, in the range of from 0.2 wt. % to 2.5 wt. %. Examples of the carrier include (or exclude) but are not limited to a solvent. Examples of other additives include (or exclude) but are not limited to surfactants, anti-foaming agents, anti-freezing agents, gelling agents, and combinations thereof. The antimicrobial composition may also comprise a pharmaceutically acceptable carrier or excipient. A pharmaceutically acceptable carrier or excipient suitable for a solid preparation such as tablets or capsules can be, for example, binders (e.g., acacia, gelatin, dextrin, hydroxypropylcellulose, methylcellulose, polyvinylpyrrolidone), solvents, dispersion media, diluents (e.g., lactose, sucrose, mannitol, corn starch, potato starch, calcium phosphate, calcium citrate, crystalline cellulose), lubricants (e.g., magnesium stearate, calcium stearate, stearic acid, talc, anhydrous silicic acid), disintegrants (e.g., corn starch, potato starch, carboxymethylcellulose, carboxymethylcellulose calcium, alginic acid), and wetting agents (e.g., sodium laurylsulfate). A pharmaceutically acceptable carrier or excipient suitable for a liquid preparation, such as solutions or suspensions, can be, for example, aqueous vehicles (e.g., water), suspending agents (e.g., acacia, gelatin, methyl cellulose, carboxymethylcellulose sodium, hydroxymethyl-cellulose, aluminum stearate gel), surfactants (e.g., lecithin, sorbitan monooleate, glycerin monostearate), and non-aqueous vehicles (e.g., glycerin, propylene glycol, vegetable oil). Moreover, liquid preparations may contain preservatives (e.g., p-hydroxybenzoic acid methyl ester, p-hydroxybenzoic acid propyl ester), flavors, and/or coloring agents. The antimicrobial composition in this disclosure can be formulated to be in any suitable form, including but not limited to liquid, gel and paste.

The present disclosure also provides a method of killing or inhibiting microbial growth, comprising applying the antimicrobial composition comprising a compound having the formula (I) or (II) as described. The antimicrobial composition or the compound is used to kill or inhibit growth of at least one group of microorganisms selected from the group consisting of bacteria, viruses, yeast, fungi, and protozoa, or to inhibit formation of a biofilm or eradicate a pre-established biofilm. Examples of a suitable method include but are not limited to pouring, spraying, any other suitable methods and any combinations thereof.

In another aspect, the present disclosure further provides a film or coating comprising a compound

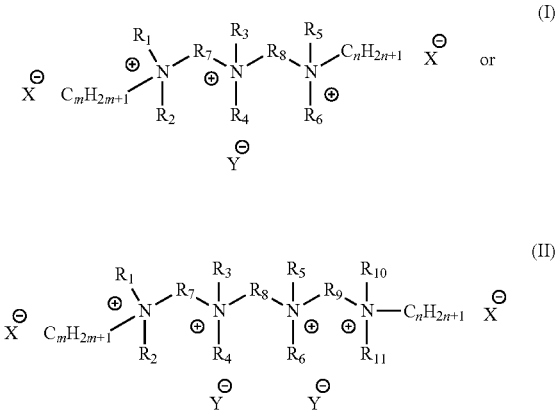

The compound having the formula (I) or (II) is grafted onto a solid surface. As described, $R_1$, $R_2$, $R_3$, $R_4$, $R_5$, $R_6$, $R_{10}$, or $R_{11}$ can be H or a $C_{1-12}$ alkyl (e.g., a $C_{2-5}$ alkyl) unsubstituted or optionally substituted with a functional group selected from the group consisting of —OH, —OR', —NH$_2$, —NHR', —NR'$_2$, —N—C(O)R', —N—C(O)CR'=CR', —SH, —SR', —O—C(O)R', —C(O)R', —CF$_3$, —OCF$_3$, halogen, benzyl, o-vinylbenzyl, m-vinylbenzyl, p-vinylbenzyl, phenyl, allyl, and substituted allyl. $R_7$, $R_8$ or $R_9$ can be a $C_{1-12}$ alkyl (e.g., a $C_{2-5}$ alkyl) unsubstituted or optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$. R' is H or a $C_{1-4}$ alkyl. X or Y is a halogen, including fluorine, chlorine, bromine, iodine and any combinations thereof. m and n are integers in the range from 1 to 25 (e.g., in the range from 10 to 16).

For example, the compound grafted on a solid surface may have a structure as shown by the formula

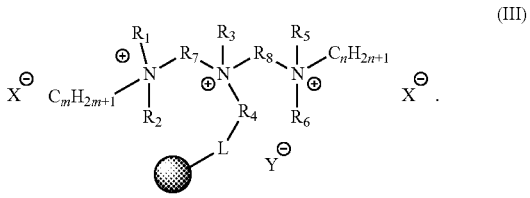

L is a linker comprising a functional group. In some embodiments, R4 is a methylene group optionally substituted with a functional group selected from the group consisting of —OH, —OR', —NH$_2$, —NHR', —NR'$_2$, —SH, —SR', —O—C(O)R', —C(O)R', —CF$_3$, and —OCF$_3$. In some embodiments, in such a film or coating comprising a compound having the formula (I) or (II), at least one of $R_1$, $R_2$, $R_3$, $R_4$, $R_5$, $R_6$, $R_{10}$, or $R_{11}$ is a $C_{1-12}$ alkyl substituted with a functional group selected from the group consisting of —SH, allyl, and substituted allyl. X can be chlorine or bromine. At least one of m and n may be 12.

The film or coating is configured to kill or inhibit growth of at least one group of microorganisms selected from the group consisting of bacteria, viruses, yeast, fungi, and protozoa, or to inhibit formation of a biofilm or eradicate pre-established biofilms.

EXAMPLES

A series of polycationic amphiphiles have been prepared. Such polycationic amphiphiles have powerful antimicrobial activities. The examples described below are for the purpose of illustration only.

1. Two Triscationic Amphiphiles for Eradicating Established Biofilm

Figure 2:
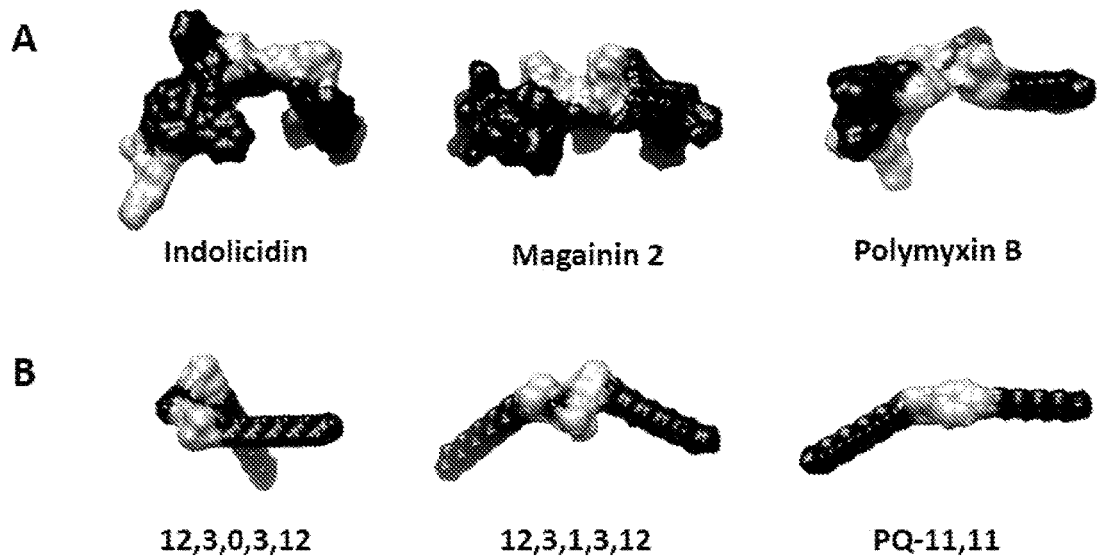
FIG. 2 illustrates the approach of mimicking antimicrobial peptides using exemplary structures (Chimera-rendered space filling models of lowest energy conformations) showing the cationic regions (light regions) and hydrophobic regions (dark regions).

Cationic amphiphiles have been implemented, both biologically and commercially, to thwart bacterial infections. In the biological arena, both eukaryotic and prokaryotic organisms exploit antimicrobial peptides (AMPs) to prevent and eliminate prokaryotic colonization. AMPs strategically incorporate a variety of features within the peptide scaffold to eradicate infections including cationic, amphipathic, and hydrophobic residues. Representative AMPs with various secondary structures (e.g. linear, alpha helical) with different physical properties (charged or hydrophobic) illustrated in different shades are depicted in FIG. 2A. In FIG. 2, the light regions are positively charged and the black regions are hydrophobic.

In contrast to inhibitors, which prevent the formation of biofilms, and dispersers, which promote the transition to planktonic cells, compounds that completely eradicate established biofilms at practical concentrations (<500 μM) have been sparsely reported. Based on this key deficiency, and inspired by previous work on antimicrobial peptides (AMP) derivatives, the inventors hypothesized that quaternary ammonium cations (QACs) could serve as simplified AMPs and eradicate pre-existing biofilms. To the best knowledge of the inventors, there have been no documented studies of their effects on biofilms.

Scheme 1 shows synthesis and structures of mono- and bis-QACs (structures 1-7',9',11' in this section), paraquat (PQ)-11,11 (structure 8'), and tris-QACs (10',12'). Tris-QACs (compounds 10',12') have been synthesized in accordance with some embodiments in the present disclosure. The QAC structures shown in Scheme 1 are reminiscent of the class of polyamines (e.g., norspermidine), and accordingly the inventors hypothesized that QACs, particularly the polycationic amphiphiles provided in the present disclosure, would possess the potent antibiofilm activity sought. Table 1 shows the minimum inhibitory concentration of the compounds illustrated in Scheme 1. Table 2 shows the minimum biofilm eradication concentration (MBEC) of these compounds.

The inventors' focused library of QACs utilized varied linker length to probe the effect that both charge and three-dimensional structure play in the compounds' biological effect, akin to the structural diversity displayed by AMPs (as shown in FIG. 2B). Recent efforts from the laboratories of the inventors led to the inexpensive preparation of tetramethylethylenediamine (TMEDA)-derived QACs with low micromolar inhibitory activity against both Gram-positive and Gram-negative planktonic bacteria (e.g., compound 12,2,12). In an extension of this TMEDA platform, the compound library was designed to include mono-, bis-, and tris-cations as well as mono-, di-, and triamines with linker lengths of two, three, and five carbons. With the exception of compound 1' (benzalkonium chloride, a component of many household antiseptics), all synthesized compounds are accessible in one to two steps from commercially available starting materials through simple alkylation chemistry (Scheme 2). The compounds bearing dodecyl side chains demonstrated MIC values in the low micromolar range (Table 1).

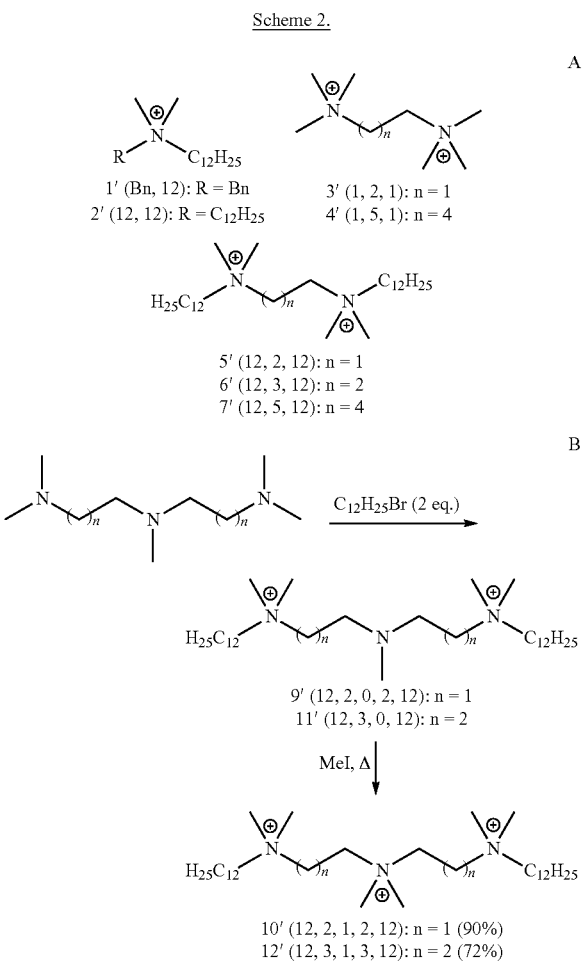

Scheme 2.

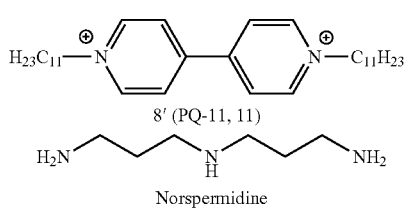

TABLE 1

MICs of norspermidine, QACs, and PQ-11,11.

| | MIC (µM) | | | |
|---|---|---|---|---|
| Compound (No.) | S. aureus | E. faecalis | E. coli | P. aeruginosa |
| Norspermidine | >500 | >500 | >500 | >500 |
| Bn,12 (1') | 8 | 8 | 32 | 63 |
| 12,12 (2') | 1 | 1 | 8 | 32 |
| 1,2,1 (3') | >500 | >500 | >500 | >500 |
| 1,5,1 (4') | >500 | >500 | >500 | >500 |
| 12,2,12 (5') | 1 | 1 | 2 | 4 |
| 12,3,12 (6') | 2 | 1 | 1 | 4 |
| 12,5,12 (7') | 1 | 1 | 1 | 4 |
| PQ-11,11 (8') | 1 | 1 | 1 | 4 |
| 12,2,0,2,12 (9') | 1 | 2 | 1 | 4 |
| 12,2,1,2,12 (10') | ≤0.25 | ≤0.25 | 0.5 | 1 |
| 12,3,0,3,12 (11') | 1 | ≤0.25 | ≤0.25 | 4 |
| 12,3,1,3,12 (12') | 0.5 | 1 | 1 | 2 |

Encouraged by the potency of the QACs against planktonic bacterial cells, the inventors then evaluated the efficacy of compound (12,2,12) against Staphylococcus aureus and Enterococcus faecalis biofilms. Compound (12,2,12) showed significant effects on pre-established biofilms at low micromolar concentrations (Table 2). To both accurately evaluate the antibiofilm activity, a regrowth assay was utilized to establish the minimum biofilm eradication concentration (MBEC) of each compound. Compound (12,2,12) has an MBEC value of 75 µM against both bacteria, approximately two-fold better than the monocationic derivative (12,12) and commercially-utilized compound 1' (Bn, 12) (Table 2.) It was also found that compounds (1,2,1) and (1,5,1) were unable to eradicate biofilms at the concentrations tested, demonstrating that both the cationic character and alkyl side chains are necessary to retain efficacy.

TABLE 2

MBECs of norspermidine, QACs, and PQ-11,11.

| | MBEC (µM) | |
|---|---|---|
| Compound (No.) | S. aureus | E. faecalis |
| Norspermidine | >200 | >200 |
| Bn,12 (1') | 200 | 200 |
| 12,12 (2') | >200 | 200 |
| 1,2,1 (3') | >200 | >200 |
| 1,5,1 (4') | >200 | >200 |
| 12,2,12 (5') | 75 ± 25$^a$ | 75 ± 25$^a$ |
| 12,3,12 (6') | 100 | 75 ± 25$^a$ |
| 12,5,12 (7') | 75 ± 25$^a$ | 75 ± 25$^a$ |
| PQ-11,11 (8') | 50 | 50 |
| 12,2,0,2,12 (9') | 75 ± 25$^a$ | 100 |
| 12,2,1,2,12 (10') | 50 | 25 |
| 12,3,0,3,12 (11') | 100 | 50 |
| 12,3,1,3,12 (12') | 100 | 50 |

$^a$MBEC values varied between 50 and 100 µM for the six trials.

Figure 3:
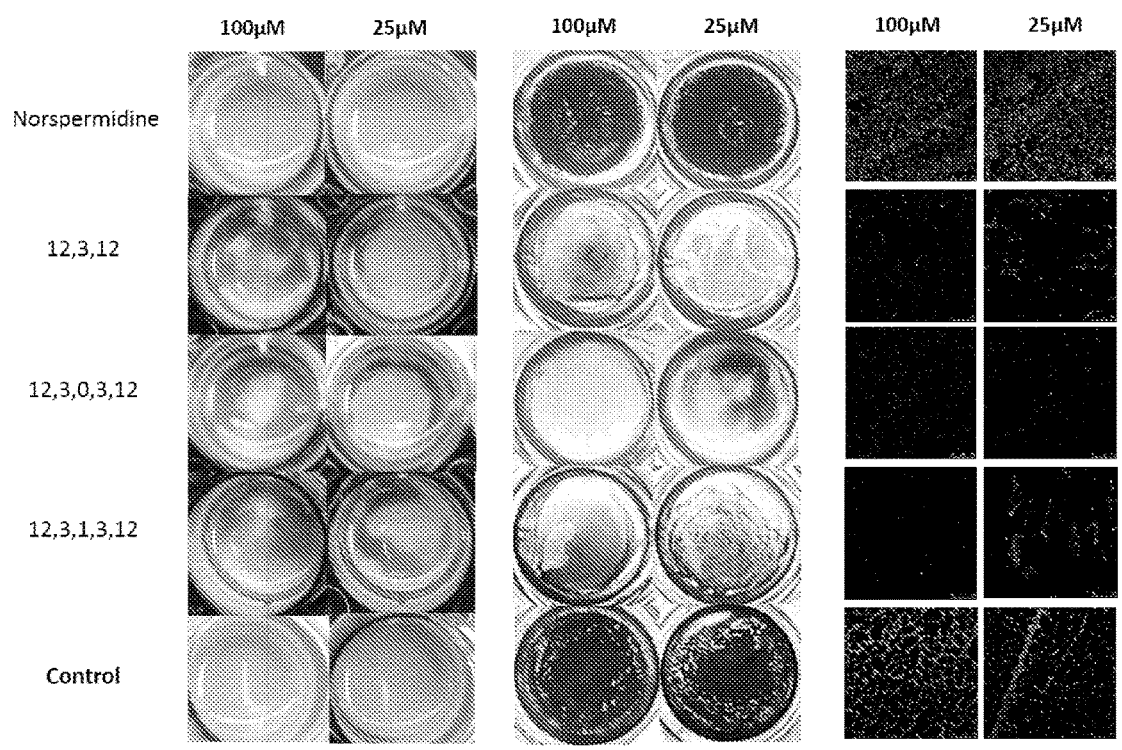
FIG. 3 shows images of crystal violet staining and confocal microscopy. Left: Submerged S. aureus biofilms 16 h post-treatment with the indicated final well concentration of compound. Middle: Biofilms stained with 1% crystal violet. Right: Confocal microscopy images of biofilms 16 h post-treatment.

The minimum biofilm eradication concentration (MBEC) of other compounds are shown in Table 2. The inventors have determined that both cationic character and alkyl side chains are important for biofilm eradication. Triscationic compounds (12,2,1,2,12) and (12,3,1,3,12) also showed good capability for film eradication. Compound (12,3,1,3, 12) and biscationic compound (12,3,0,3,12) showed similar results. There is a moderate increase in efficacy between bis-cation (12,2,0,2,12) and tris-cation (12,3,0,3,12) that provides the most active biofilm-eradicating compound reported among these compound. To demonstrate the activity of these compounds, crystal violet staining and confocal imaging was utilized (FIG. 3). Crystal violet staining illustrates the significant effect that QACs (12,3,12), (12,3,0,3, 12), and (12,3,1,3,12) display against pre-established biofilms when compared to the aqueous control or norspermidine. Furthermore, confocal microscopy reveals significant biofilm perturbation at concentrations as low as 12 µM, significantly lower than the reported MBEC values.

In summary, the inventors have demonstrated for the first time that QACs, are potent eradicators of pre-established bacterial biofilms. This development also provides insight toward the minimal structural features needed to eradicate *S. aureus* and *E. faecalis* biofilms; merely two permanent cationic charges with alkyl side chains can confer biofilm disruption capability. The compounds are synthesized in one or two steps from commercially available material, making them attractive alternatives to existing methods for biofilm eradication. Triscationic amphiphiles including (12,2,1,2, 12) and (12,3,1,3,12) show remarkable antibiofilm activity.

2. Additional Triscationic and Tetracationic Amphiphiles and their Antimicrobial Activities Despite numerous reports of the antimicrobial activity of biscationic amphiphiles, there are no investigations to the inventors' knowledge correlating antimicrobial activity to amphiphiles with three or four quaternary ammonium groups. This stands in stark contrast to the wide variety of bioactive natural products (and derivatives thereof) incorporating multiple primary, secondary, and tertiary amines; common examples include spermine, spermidine, squalamine, and others. While these are generally drawn as neutral compounds, they will have multiple cations at physiological pH; related compounds have been investigated as possible biofilm disruptors.

With the ready availability of compounds with three or four tertiary amines at modest commercial cost, the inventors continued correlating bioactivity to amphiphilic structure, specifically the number of cations present, as well as the number and lengths of non-polar side chains. The target set of compounds is summarized in Scheme 3. For the trisamine-inspired structures, compounds were designed with either a five- or seven-atom linker between two quaternary ammonium species (Scheme 3, left). This allows for the incorporation of an additional quaternary ammonium moiety in the center of the structure, which can be attached to either short or long chain alkyl residues. The inventors also aimed to prepare structures based on a tetraamine platform, bearing up to four ammonium residues (Scheme 3, right). The inventors aimed to develop unified synthetic methods for the amphiphiles presented.

Scheme 3.

triamine structures

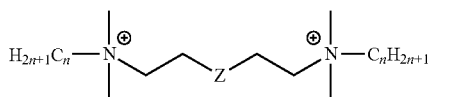

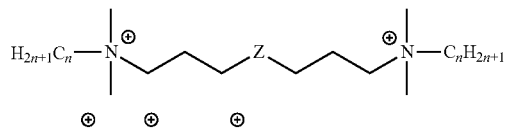

$Z = CH_2, NCH_3, N(CH_3)_2, N(CH_3)allyl, N(CH_3)R$ tetraamine structures

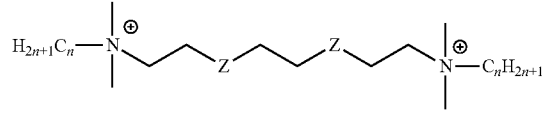

$Z = NCH_3, N(CH_3)_2, N(CH_3)allyl$

The inventors first set out to assemble a set of structures that were strictly biscationic, using the simple n,5,n structures, ($Z=CH_2$, Scheme 3), where n is the length of alkyl chains, and five is the linker length between the nitrogen atoms. Scheme 4 illustrates the preparation of biscationic amphiphiles of the n,5,n series. Syntheses, as illustrated in Scheme 4, were accomplished by the exposure of 1,5-dibromopentane to a range of dimethyl alkyl amines, providing compounds 1-4 (described below in this section). Yields ranged from 72 to 90%. The bis-alkylated products were recrystallized as necessary to remove any residual starting material or alkyl bromide and provide compounds in high purity.

Scheme 4.

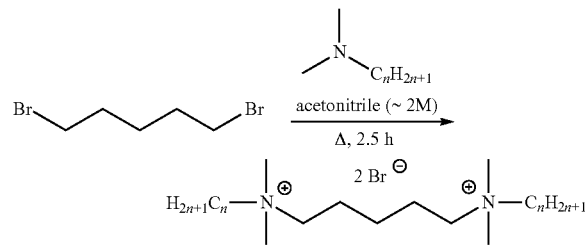

n, 5, n
1, 10, 5, 10, n = 10; 76%
2, 12, 5, 12, n = 12; 80%
3, 14, 5, 14, n = 14; 72%
4, 16, 5, 16, n = 16; 90%

Scheme 5 illustrates preparation of amphiphiles of the (n,2,0,2,n) series. In preparation for a series of compounds bearing either two or three cationic species, the inventors began with the inexpensive pentamethyl bis(ethylenediamine) as shown in Scheme 5. Alkylation thereof was found to be both selective and high-yielding, providing five structures of the (n,2,0,2,n) series, where n is the length of alkyl chains, 2 is the linker length between the nitrogens, and 0 represents the lack of additional substitution on the central nitrogen.

Scheme 5.

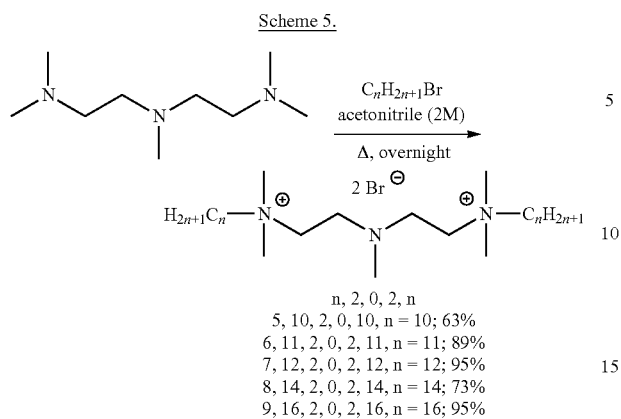

n, 2, 0, 2, n
5, 10, 2, 0, 10, n = 10; 63%
6, 11, 2, 0, 2, 11, n = 11; 89%
7, 12, 2, 0, 2, 12, n = 12; 95%
8, 14, 2, 0, 2, 14, n = 14; 73%
9, 16, 2, 0, 2, 16, n = 16; 95%

Synthesis of an exemplary compound (14,2,0,2,14) is described herein as representative procedure of preparing compound (m, 2,0, 2,n). To a solution of 1-bromotetradecane (2.25 mL, 8.26 mmol) in $CH_3CN$ (2 mL) was added N,N,N',N'',N''-pentamethyldiethylenetriamine (0.87 mL, 4.2 mmol). The resulting clear solution was stirred at rt for 20 h, during which time a white solid was observed. To the reaction mixture was added cold acetone (~9 mL), which led to a white precipitate. Filtration through a Buchner funnel furnished a white solid, which was washed with cold acetone (~4 mL) and then hexanes (~4 mL), affording (14,2,0,2,14) (2.188 g, 73%) as a white solid.

Further functionalization of compounds of the n,2,0,2,n series was not as straightforward as the inventors had hoped, as attempted alkylation with long-chained electrophiles (e.g., dodecyl bromide) proved sluggish. However, the inventors were able to effect alkylations (Scheme 6) under stronger conditions, either in neat iodomethane at room temperature (7d, providing n,2,1,2,n) or in allyl bromide at reflux (overnight, providing n,2,3A,2,n). Methylation yields were high (≥90%), and allylation yields were good (46-83%). Scheme 6 illustrates the preparation of amphiphiles of the type (n,2,1,2,n) and (n,2,3A,2,n).

Scheme 6.

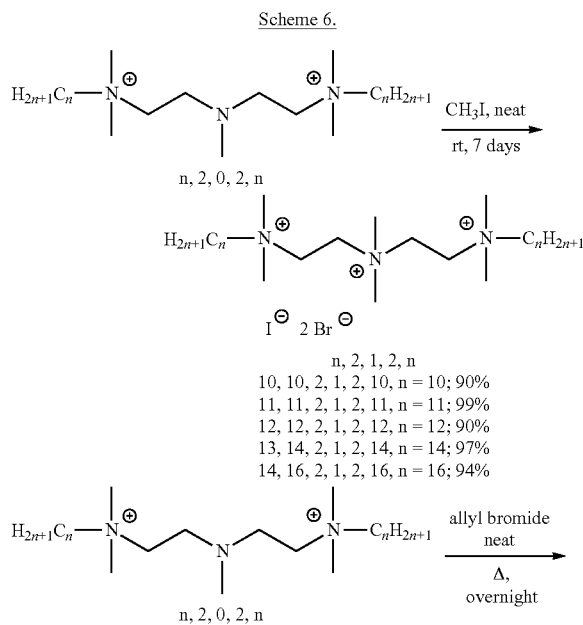

n, 2, 0, 2, n n, 2, 1, 2, n
10, 10, 2, 1, 2, 10, n = 10; 90%
11, 11, 2, 1, 2, 11, n = 11; 99%
12, 12, 2, 1, 2, 12, n = 12; 90%
13, 14, 2, 1, 2, 14, n = 14; 97%
14, 16, 2, 1, 2, 16, n = 16; 94%

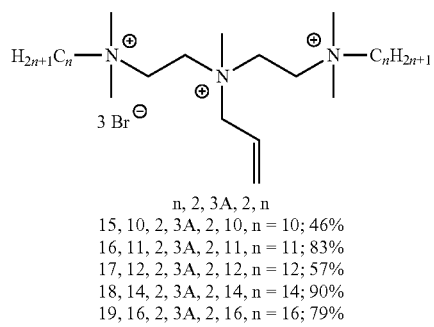

n, 2, 3A, 2, n
15, 10, 2, 3A, 2, 10, n = 10; 46%
16, 11, 2, 3A, 2, 11, n = 11; 83%
17, 12, 2, 3A, 2, 12, n = 12; 57%
18, 14, 2, 3A, 2, 14, n = 14; 90%
19, 16, 2, 3A, 2, 16, n = 16; 79%

Synthesis of an exemplary compound (12,2,1,2,12) is described herein as representative procedure of preparing compound (m, 2,1, 2, n). To a solution of $CH_3I$ (~1.0 mL, 16 mmol) was added (12,2,0,2,12) (201 mg, 0.299 mmol). The resulting clear yellow solution was stirred at room, and additional $CH_3I$ was added over 72 hours, during which time a solid was observed. Crude $^1H$ NMR showed that (12,2,1, 2,12) was the major product.

Scheme 7 shows the preparation of amphiphiles with 7-atom linkers of the type (12,7,12) and (12,3,x,3,12). Suspecting that the proximity of the three cationic nitrogens was an impediment to this final alkylation, the inventors prepared an analogous set of compounds with seven-atom linkers between the "bookend" quaternary ammonium species, maintaining the dodecyl side chains. This began with the preparation of (12,7,12) (Scheme 7) in accordance with the method above. Then, starting with known amphiphile (12,3,0,3,12) (derived from commercially available 2,6,10-trimethyl-2,6,10-triazaundecane) we were able to prepare a set of structures with varied substitution at the center carbon. The inventors first prepared substitutions of methyl and allyl (12,3,1,3,12) and (12,3,3A,3,12), respectively, to parallel the above compounds (12,2,1,2,12) and (12,2,3A,2,12). Simple alkylation was accomplished in good yield with both butyl and dodecyl chains (12,3,4,3,12) and (12,3,12,3,12), respectively, from reflux with the corresponding alkyl bromide. Additionally, both benzyl and para-octyl benzyl groups were prepared as well.

Scheme 7.

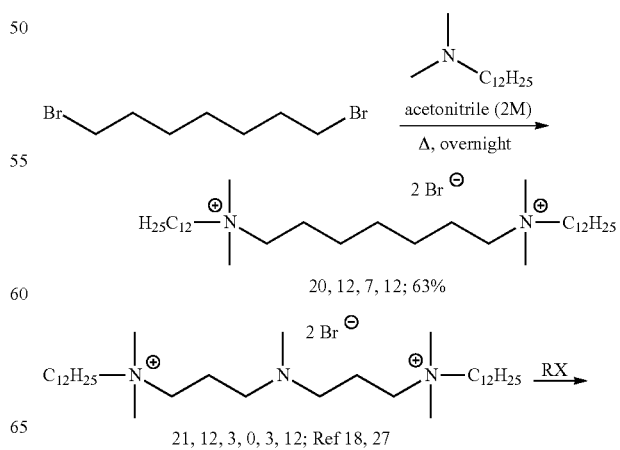

20, 12, 7, 12; 63%

21, 12, 3, 0, 3, 12; Ref 18, 27

-continued

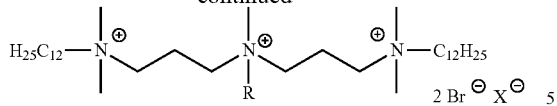

$2\text{Br}^\ominus \text{X}^\ominus$ 22, 12, 3, 1, 3, 12, R = CH₃; X = I⁻; 72%
23, 12, 3, 3A, 3, 12, R = allyl; X = Br⁻; 83%
24, 12, 3, 4, 3, 12, R = butyl; X = Br⁻; 51%
25, 12, 3, Bn, 3, 12, R = benzyl; X = Br⁻; 94%
26, 12, 3, Bn-8, 3, 12, R = p-octylbenzyl; X = Br⁻; 49%
27, 12, 3, 12, 3, 12, R = dodecyl; X = Br⁻; 78%

Scheme 8 illustrates the preparation of amphiphiles of the type (N4-n,n,n,n). To further extend the scope of the investigation, the inventors prepared a series of compounds bearing four amines, starting with the commercially available 1,1,4,7,10,10-hexamethyltriethylenetetramine (abbreviated as N4-0,0,0,0), shown in Scheme 8. This opened the possibility of evaluating amphiphiles with up to four cations. The inventors found that monoalkylation of (N4-0,0,0,0) was somewhat selective under our standard conditions (1 equiv RBr, acetonitrile, Δ), providing (N4-12,0,0,0) and (N4-14,0,0,0) in 53-65% yield after trituration. Subsequent alkylation of 29 with 1 equivalent of dodecyl bromide led to a clean preparation of the pseudoasymmetric (N4-14,0,0,12), wherein solely the peripheral nitrogens were alkylated, as evidenced by NMR spectra that displayed high levels of symmetry. Alternatively, bis-alkylation of the starting tetraamine furnished either (N4-12,0,0,12) or (N4-14,0,0,14) (93 and 84%, respectively). Bis-ammonium compound N4-12,0,0,12 was in turn bis-allylated under forcing conditions (neat allyl bromide, reflux, 2.5 h) to provide a tetracationic derivative (N4-12,3A,3A,12) (91%).

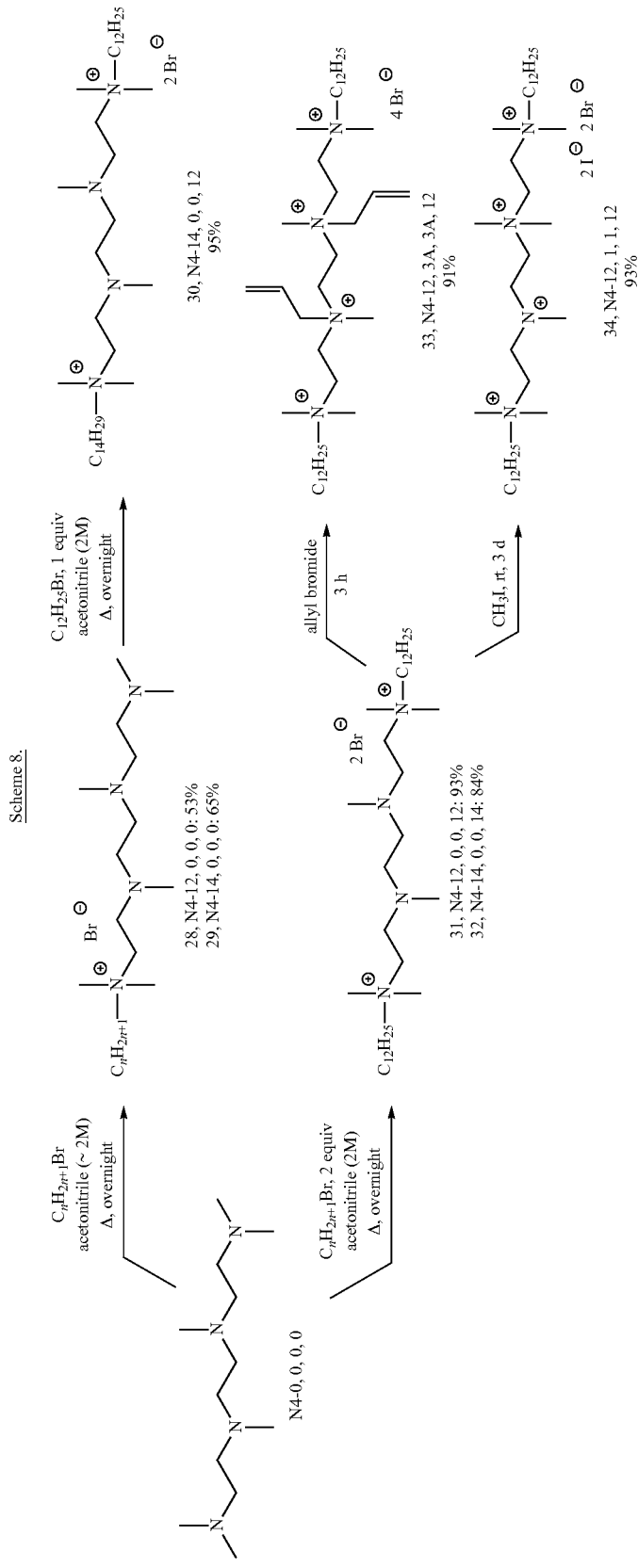

With nearly three-dozen amphiphiles varying in structure and cationic nature synthesized, minimum inhibitory concentration (MIC) values against the Gram-positive *Staphylococcus aureus* and *Enterococcus faecalis* and the Gram-negative *Escherichia coli* and *Pseudomonas aeruginosa* were determined by standard methods. Table 3 shows the MIC values for prepared amphiphilic compounds, reported in M. The commercially available antibacterial agent benzalkonium chloride (benzyldimethyldodecylammonium chloride, Bn, 12) was tested for comparison. The broth microdilution for determining MIC values was performed as previously reported.

compounds with 1, 2, or 4 ammonium groups (e.g., N4-12, 0,0,0, N4-12,0,0,12, and N4-12,3A,3A,12). While (N4-12, 3A,3A,12) did indeed show strong activity (MIC values=1 μM versus three bacteria, and 2 μM versus *P. aeruginosa*), N4-12,0,0,12 was equally active, excepting a value of 4 μM versus *P. aeruginosa*. These both were about 8-fold more bioactive than (N4-12,0,0,0), which bears just one quaternary ammonium group.

In summary, polycationic amphiphiles provided in this disclosure provide great ability to disrupt persistent biofilms and display some level of preferential activity at the more anionic membrane of prokaryotes.

TABLE 3

| No. | Compound | Charge (# nitrogens) | S. aureus | E. faecalis | E. coli | P. aeruginosa |
|---|---|---|---|---|---|---|
| 1 | 10, 5, 10 | 2+ (2N) | 2 | 4 | 8 | 63 |
| 2 | 12, 5, 12 | 2+ (2N) | 2 | 1 | 1 | 2 |
| 3 | 14, 5, 14 | 2+ (2N) | 1 | 1 | 4 | 16 |
| 4 | 16, 5, 16 | 2+ (2N) | 2 | 2 | 16 | 32 |
| 5 | 10, 2, 0, 2, 10 | 2+ (3N) | 2 | 8 | 8 | 63 |
| 6 | 11, 2, 0, 2, 11 | 2+ (3N) | 2 | 2 | 2 | 8 |
| 7 | 12, 2, 0, 2, 12 | 2+ (3N) | 1 | 1 | 2 | 4 |
| 8 | 14, 2, 0, 2, 14 | 2+ (3N) | 2 | 1 | 4 | 16 |
| 9 | 16, 2, 0, 2, 16 | 2+ (3N) | 4 | 2 | 16 | 32 |
| 10 | 10, 2, 1, 2, 10 | 3+ (3N) | 2 | 8 | 8 | 63 |
| 11 | 11, 2, 1, 2, 11 | 3+ (3N) | 2 | 2 | 4 | 8 |
| 12 | 12, 2, 1, 2, 12 | 3+ (3N) | ≤0.25-4$^a$ | ≤0.25-4$^a$ | 0.5-4$^a$ | 1-8$^a$ |
| 13 | 14, 2, 1, 2, 14 | 3+ (3N) | 1 | 1 | 2 | 8 |
| 14 | 16, 2, 1, 2, 16 | 3+ (3N) | NT | NT | NT | NT |
| 15 | 10, 2, 3A, 2, 10 | 3+ (3N) | 2 | 4 | 2 | 63 |
| 16 | 11, 2, 3A, 2, 11 | 3+ (3N) | 1 | 2 | 2 | 16 |
| 17 | 12, 2, 3A, 2, 12 | 3+ (3N) | 2 | 2 | 2 | 4 |
| 18 | 14, 2, 3A, 2, 14 | 3+ (3N) | 2 | 2 | 2 | 8 |
| 19 | 16, 2, 3A, 2, 16 | 3+ (3N) | 4 | 4 | 8 | 16 |
| 20 | 12, 7, 12 | 2+ (2N) | 1 | 1 | 2 | 8 |
| 21 | 12, 3, 0, 3, 12 | 2+ (3N) | 1 | 2 | 1 | 4 |
| 22 | 12, 3, 1, 3, 12 | 3+ (3N) | 1 | 2 | 2 | 8 |
| 23 | 12, 3, 3A, 3, 12 | 3+ (3N) | 1 | 2 | 2 | 4 |
| 24 | 12, 3, 4, 3, 12 | 3+ (3N) | 1 | 1 | 1 | 2 |
| 25 | 12, 3, Bn, 3, 12 | 3+ (3N) | 1 | 1 | 1 | 2 |
| 26 | 12, 3, Bn-8, 3, 12 | 3+ (3N) | 1 | 1 | 1 | 4 |
| 27 | 12, 3, 12, 3, 12 | 3+ (3N) | 0.5 | 1 | 1 | 4 |
| 28 | N4-12, 0, 0, 0 | 1+ (4N) | 8 | 8 | 8 | 32 |
| 29 | N4-14, 0, 0, 0 | 1+ (4N) | 16 | 16 | 32 | 125 |
| 30 | N4-14, 0, 0, 12 | 2+ (4N) | 1 | 1 | 2 | 8 |
| 31 | N4-12, 0, 0, 12 | 2+ (4N) | 1 | 1 | 1 | 4 |
| 32 | N4-14, 0, 0, 14 | 2+ (4N) | 2 | 1 | 2 | 16 |
| 33 | N4-12, 3A, 3A, 12 | 4+ (4N) | 1 | 1 | 1 | 2 |
| 34 | N4-12, 1, 1, 12 | 4+ (4N) | NT | NT | NT | NT |
| — | Bn, 12 | 1+ (1N) | 8 | 8 | 32 | 63 |

$^a$Compound (12, 2, 1, 2, 12) showed modest water solubility, and thus provided varying MIC values.

The MIC data obtained for the 32 amphiphiles tested were found to be remarkably consistent, with over half of compounds tested (20/32) displaying single digit MICs versus all four bacteria tested. MIC variation mostly hinged on the length of alkyl chain, where the dodecyl chain was generally found to be optimal. This was exemplified in the comparison of the X=CH$_2$ compounds, in both the n,5,n series (1-4) as well as (12,7,12) (20), to the corresponding structures bearing the N—CH$_3$ group (5, 7-9, 21) or quaternary ammonium groups (10, 12-13, 22, etc) in the center of the compound; little was changed across the board. In fact, (12,5,12) and (12,7,12) were two of the most potent compounds we prepared, with MIC values≤2 μM in 7 of the 8 cases tested. Compound (12,2,1,2,12) was found to be sparingly soluble in water, and thus posed difficulty in providing repeatable MIC values. In light of the result that longer linkers provided comparable activity, the inventors evaluated the greater structural variety available in the (12,3,x,3,12) series. Finally, the tetraamine scaffold allowed for comparison of 3. Exemplary Compound (12,3,2,3,12)

An exemplary compound (12,3,2,3,12) was prepared through a two-step process.

Step 1: Preparation of Compound (12,3,0,3,12)

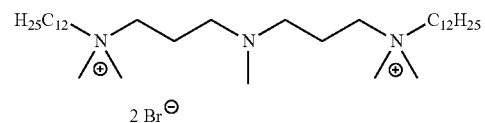

To a solution of 2,6,10-trimethyl-2,6,10-triazaundecane (2.77 mL, 2.30 g, 11.4 mmol) in acetonitrile (2.0 mL) was added 1-bromododecane (5.45 mL, 5.66 g, 22.7 mmol). The resulting colorless solution was heated to reflux for 48 h, during which time a golden paste was observed. After cooling, hexane (~15 mL) was added to the reaction mixture. Filtration though a Büchner funnel furnished a yellow-gold gel, which was washed with cold hexanes (~5 mL) to afford compound (12,3,0,3,12) (7.95 g, ~100%) as a yellow-gold gel.

Step 2: Preparation of Compound (12,3,2,3,12).

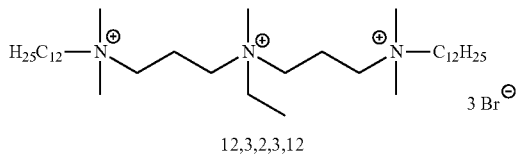

12,3,2,3,12

To the semi-solid trisamine (12,3,0,3,12) (572.3 mg, 0.818 mmol) was added bromoethane (2 mL, 26 mmol). The resulting pale yellow-orange solution was warmed to reflux with stirring for 22 h, during which time a white precipitate was observed. After addition of cold acetone (10 mL) to the still-warm reaction flask, the precipitate was filtered through a Büchner funnel, rinsing with cold acetone (3 mL), before being dried in vacuum, affording 12,3,2,3,12 as a white powder (0.5438 g, 82%), as a white solid; mp=217-219° C.; $^1$H NMR (300 MHz, CDCl$_3$) δ 3.91 (s, 4H), 3.79 (s, 8H), 3.47-3.36 (m, 17H), 2.58 (s, 4H), 1.77 (s, 4H), 1.50 (t, 3H), 1.33-1.16 (m, 36H), 0.86 (t, 6H); $^{13}$C NMR (75 MHz, CDCl$_3$) δ 66.39, 61.18, 57.53, 51.04, 49.27, 31.86, 29.59, 29.51, 29.47, 29.28, 26.37, 22.96, 22.62, 18.32, 14.04, 9.02.

Compound (12,3,2,3,12) has showed excellent antimicrobial activities. For example, the values of the MIC (in μM) and the MBEC for each bacterium evaluated are as follows:

| Bacteria | MICs (μM): |
|---|---|
| S. aureus (SH1000) | 0.5 |
| E. faecalis (OG1RF) | 0.5 |
| E. coli (MC4100) | 1 |
| P. aeruginosa (PA01) | 2 |
| CA-MRSA (USA300-0114) | 0.5 |
| HA-MRSA (ATCC33591) | 1 |

| Bacteria | MBECs (μM) |
|---|---|
| S. aureus | 100 |
| E. faecalis | 100 |
| USA300-0114 | 100 |
| Lysis20: | 8 |

No resistance was observed in liquid cultures of SH1000 or USA300-0114 serially passaged with Compound (12,3,2,3,12) over a period of at least 14 days.

4. Exemplary Compound (12,3,11-SH,3,12)

An exemplary compound (12,3,11-SH,3,12) having the following formula was prepared as follows.

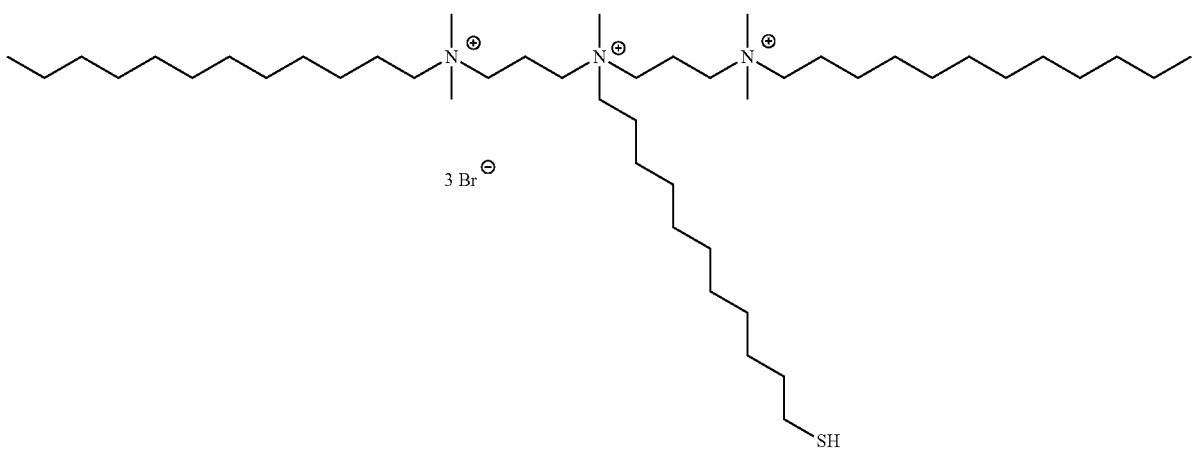 [SMILES: CCCCCCCCCCCC[N+](C)(C)CCC[N+](C)(CCCCCCCCCCCS)CCC[N+](C)(C)CCCCCCCCCCCC]

To a solution of 11-bromo-1-undecanethiol (0.1250 g, 0.4677 mmol) in acetonitrile (~1 mL) was added 12,3,0,3,12 (0.3273 g, 0.4538 mmol). The resulting colorless solution was heated at reflux under argon for 1 week. Addition acetonitrile (1 mL) was added to the reaction flask after 2 days and 3 days to facilitate dissolution. To the warm reaction mixture was added cold hexanes (~6 mL), during which time a yellowish precipitate was observed. Filtration through a Büchner funnel furnished a yellowish amorphous solid, which was washed with cold hexanes (~10 mL) to afford 12,3,11-SH,3,12 (0.170 g, 80%) as a yellow amorphous solid; $^1$H NMR (300 MHz, CDCl$_3$) δ 3.73 (s, 8H), 3.42 (s, 6H), 3.33-3.27 (m, 15H), 3.09 (s, 1H) 2.45-2.40 (m, 6H), 1.72 (s, 6H), 1.56-1.48 (m, 6H), 1.29-1.19 (m, 46H), 0.81 (t, J=6.5 Hz, 6H); $^{13}$C NMR (75 MHz, CDCl$_3$) δ 66.19, 66.02, 64.21, 61.55, 60.92, 58.07, 51.73, 51.18, 50.95, 50.02, 41.56, 33.94, 32.15, 31.83, 29.66, 29.57, 29.27, 28.96, 28.85, 28.27, 26.32, 24.55, 22.88, 22.59, 18.67, 18.29, 14.01; high resolution mass spectrum (ESI) m/z 242.2514 ([M]$^{3+}$; calculated for [C$_{46}$H$_{100}$N$_3$S]$^{3+}$: 242.2541).

This compound (12,3,11-SH,3,12) has showed excellent antimicrobial activities. For example, the values of the MIC (in μM) and the MBEC for each bacterium evaluated are as follows:

| Bacteria | MICs (μM): |
|---|---|
| S. aureus | 2 |
| E. faecalis | 2 |

-continued

| Bacteria | MICs (µM): |
|---|---|
| E. coli | 2 |
| P. aeruginosa | 8 |
| USA300-0114 | 2 |
| ATCC 33591 | 2 |

| Bacteria | MBECs (µM): |
|---|---|
| S. aureus | 200 |
| E. faecalis | >200 |
| USA300-0114 | >200 |

Although the subject matter has been described in terms of exemplary embodiments, it is not limited thereto. Rather, the appended claims should be construed broadly, to include other variants and embodiments, which may be made by those skilled in the art.

What is claimed is:

1. An antimicrobial composition comprising a compound having the formula $$\text{(I)}$$

$$\text{(II)}$$

wherein:
$R_1$, $R_2$, $R_3$, $R_4$, $R_5$, $R_6$, $R_{10}$, or $R_{11}$ is H or a $C_{1-12}$ alkyl unsubstituted or optionally substituted with a functional group selected from the group consisting of —NH$_2$, —NHR', —NR'$_2$, —N—C(O)R', —N—C(O)CR'=CR', —SH, —SR', —O—C(O)R', —C(O)R', —CF$_3$, —OCF$_3$, halogen, benzyl, o-vinylbenzyl, m-vinylbenzyl, p-vinylbenzyl, phenyl, allyl, and substituted allyl;
$R_7$, $R_8$ or $R_9$ is a $C_{3-12}$ alkyl unsubstituted or optionally substituted with a functional group selected from the group consisting of —NH$_2$, —NHR', —NR'$_2$, —SH, —SR', —O—C(O)R', —C(O)R', —CF$_3$, and —OCF$_3$;
R' is H or a $C_{1-4}$ alkyl;
X or Y is a halogen; and
m and n are integers in the range of from 5 to 25.

2. The antimicrobial composition of claim 1, wherein $R_7$, $R_8$ or $R_9$ is a $C_{3-5}$ alkyl unsubstituted or optionally substituted.

3. The antimicrobial composition of claim 1, wherein $R_1$, $R_2$, $R_3$, $R_4$, $R_5$, $R_6$, $R_{10}$, or $R_{11}$ is H or a $C_{1-4}$ alkyl.

4. The antimicrobial composition of claim 1, wherein at least one of $R_1$, $R_2$, $R_3$, $R_4$, $R_5$, $R_6$, $R_{10}$, or $R_{11}$ is a $C_{1-12}$ alkyl substituted with a functional group selected from the group consisting of —SH, allyl, and substituted allyl.

5. The antimicrobial composition of claim 1, wherein X or Y is chlorine or bromine.

6. The antimicrobial composition of claim 1, wherein m and n are integers in the range from 10 to 16.

7. The antimicrobial composition of claim 1, wherein at least one of m and n is 12.

8. The antimicrobial composition of claim 1, wherein the compound has the formula $$\text{(I-3)}$$

9. The antimicrobial composition of claim 8, wherein in the compound having the formula (I-3), at least one of $R_1$ and $R_2$, and at least one of $R_3$ and $R_4$, and at least one of $R_5$ and $R_6$ are methyl.

10. The antimicrobial composition of claim 8, wherein in the compound having the formula (I-3), m and n are 12, one of $R_3$ and $R_4$ is selected from a group consisting of ethyl, propyl and allyl, and the other groups among $R_1$, $R_2$, $R_3$, $R_4$, $R_5$, and $R_6$ are methyl.

11. The antimicrobial composition of claim 1, wherein the compound has the formula $$\text{(II-2)}$$

$$\text{(II-3)}$$

12. The antimicrobial composition of claim 11, wherein in the compound having the formula (II-2) or (II-3), at least one of $R_1$ and $R_2$, and at least one of $R_3$ and $R_4$, at least one of $R_5$ and $R_6$, and at least one of $R_{10}$ and $R_{11}$ are methyl.

13. The antimicrobial composition of claim 11, wherein in the compound having the formula (II-2), m and n are 12, one of $R_3$ and $R_4$ is selected from a group consisting of ethyl, propyl and allyl, and the other groups among $R_1$, $R_2$, $R_3$, $R_4$, $R_5$, $R_6$, $R_{10}$, and $R_{11}$ are methyl.

14. A method of making the antimicrobial composition of claim 1 comprising mixing an effective amount of a compound having the formula (I) or (II) and a carrier.

15. A method of killing or inhibiting microbial growth, comprising applying the antimicrobial composition of claim 1 comprising a compound having the formula (I) or (II).

16. The method of claim 15, wherein the antimicrobial composition is used to kill or inhibit growth of at least one group of microorganisms selected from the group consisting of bacteria, viruses, yeast, fungi, and protozoa, or to inhibit formation of a biofilm or eradicate a pre-established biofilm.

17. A film or coating comprising a compound

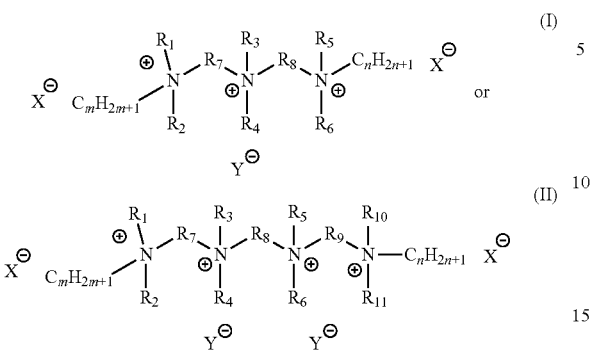

grafted onto a solid surface
wherein:
- $R_1$, $R_2$, $R_3$, $R_4$, $R_5$, $R_6$, $R_{10}$, or $R_{11}$ is H or a $C_{1-12}$ alkyl unsubstituted or optionally substituted with a functional group selected from the group consisting of —$NH_2$, —NHR', —NR'$_2$, —N—C(O)R', —N—C(O)CR'=CR', —SH, —SR', —O—C(O)R', —C(O)R', —$CF_3$, —$OCF_3$, halogen, benzyl, o-vinylbenzyl, m-vinylbenzyl, p-vinylbenzyl, phenyl, allyl, and substituted allyl;
- $R_7$, $R_8$ or $R_9$ is a $C_{3-12}$ alkyl unsubstituted or optionally substituted with a functional group selected from the group consisting of —$NH_2$, —NHR', —NR'$_2$, —SH, —SR', —O—C(O)R', —C(O)R', —$CF_3$, and —$OCF_3$;
- R' is H or a $C_{1-4}$ alkyl;
- X or Y is a halogen; and
- m and n are integers in the range of from 5 to 25.

18. The film or coating of claim 17, wherein the compound grafted on a solid surface has a structure:

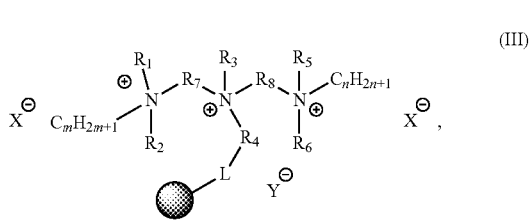

wherein L is a linker comprising a functional group.

19. The film or coating of claim 18, wherein $R_4$ is a methylene group optionally substituted with a functional group selected from the group consisting of —OH, —OR', —$NH_2$, —NHR', —NR'$_2$, —SH, —SR', —O—C(O)R', —C(O)R', —$CF_3$, and —$OCF_3$.

20. The film or coating of claim 17, wherein
$R_7$, $R_8$ or $R_9$ is a $C_{3-5}$ alkyl unsubstituted or optionally substituted.

21. The film or coating of claim 17, wherein
$R_1$, $R_2$, $R_3$, $R_4$, $R_5$, $R_6$, $R_{10}$, or $R_{11}$ is H or a $C_{1-4}$ alkyl.

22. The film or coating of claim 17, wherein
at least one of $R_1$, $R_2$, $R_3$, $R_4$, $R_5$, $R_6$, $R_{10}$, or $R_{11}$ is a $C_{1-12}$ alkyl substituted with a functional group selected from the group consisting of —SH, allyl, and substituted allyl.

23. The film or coating of claim 17, wherein
X or Y is chlorine or bromine.

24. The film or coating of claim 17, wherein
m and n are integers in the range from 10 to 16.

25. The film or coating of claim 17, wherein
at least one of m and n is 12.

* * * * *